(12) United States Patent
Beria et al.

(10) Patent No.: US 9,828,405 B2
(45) Date of Patent: Nov. 28, 2017

(54) MORPHOLINYL ANTHRACYCLINE DERIVATIVES

(71) Applicant: NERVIANO MEDICAL SCIENCES S.R.L., Nerviano (MI) (IT)

(72) Inventors: Italo Beria, Nerviano (IT); Michele Caruso, Milan (IT); Vittoria Lupi, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 91 days.

(21) Appl. No.: 14/787,667

(22) PCT Filed: Apr. 23, 2014

(86) PCT No.: PCT/EP2014/058262
§ 371 (c)(1),
(2) Date: Oct. 28, 2015

(87) PCT Pub. No.: WO2014/177441
PCT Pub. Date: Nov. 6, 2014

(65) Prior Publication Data
US 2016/0075730 A1    Mar. 17, 2016

(30) Foreign Application Priority Data
Apr. 29, 2013    (EP) .................................... 13165707

(51) Int. Cl.
| *A01N 43/04* | (2006.01) |
| *A61K 31/70* | (2006.01) |
| *C07H 9/00* | (2006.01) |
| *C07D 498/14* | (2006.01) |
| *A61K 45/06* | (2006.01) |
| *A61K 31/704* | (2006.01) |
| *A61K 31/7034* | (2006.01) |

(52) U.S. Cl.
CPC ............ *C07H 9/00* (2013.01); *A61K 31/704* (2013.01); *A61K 45/06* (2013.01); *C07D 498/14* (2013.01); *A61K 31/7034* (2013.01)

(58) Field of Classification Search
None
See application file for complete search history.

(56) References Cited

U.S. PATENT DOCUMENTS

| 3,803,124 A | 4/1974 | Arcamone |
| 4,133,877 A | 1/1979 | Masi et al. |

FOREIGN PATENT DOCUMENTS

| EP | 0288268 A2 | 10/1988 |
| EP | 0381989 A1 | 8/1990 |
| GB | 2215332 A | 9/1989 |
| GB | 2225781 A | 6/1990 |
| GB | 2247885 A | 3/1992 |
| GB | 2296495 A | 7/1996 |
| WO | WO 90/10639 A2 | 9/1990 |
| WO | WO 91/09046 A1 | 6/1991 |
| WO | WO 98/02446 A1 | 1/1998 |
| WO | WO 2012/073217 | 6/2012 |

OTHER PUBLICATIONS

Streeter et al. Cancer Chemother. Pharmacol. (1985), vol. 1, pp. 160-164.*
Arcamone E et al., "Synthesis and Biological Evaluation of Some 14-O-Acyl Derivatives of Adriamycin", Journal of Medicinal Chemistry 17(3):335-337 (1974).
Bachur N.R., "Free Radical Damage", Anthracycline Antibiotics in Cancer Therapy, pp. 97-102 (1982).
Baker T.S. et al., "Preparation and Antigenic Properties of 5a-Dihydrotestosterone-11-(O-Carboxymethyl) Oxime-BSA Conjugate", Steroids 29(4):429-441 (Apr. 1977).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Filimonov S.I. et al., "Convenient Synthesis of Novel 5-Substituted 3-Methylisoxazole-4-Sulfonamides", J. Heterocyclic Chem. 43:663-671 (May-Jun. 2006).
Fukuoka S. et al., "A Novel Catalytic Synthesis of Carbamates by Oxidative Alkoxycarbonylation of Amines in the Presence of Palladium and Iodide", J. Chem. Soc. Chem. Commun. 6:399-400 (1984).
Gopalsamy A. et al., "Pyrazolo[1,5-a]Pyrimidin-7-yl Phenyl Amides as Novel Anti-Proliferative Agents: Parallel Synthesis for Lead Optimization of Amide Region", Bioorganic & Medicinal Chemistry Letters 15:1591-1594 (2005).
Ismailov V.M. et al., "Condensation of Aniline and O-Hydroxyaniline With 1,2-Dibromoethane", Russian Journal of Organic Chemistry 40(2):284-285 (2004).
Lee Y S et al., "3,4-Dihydroquinazoline Derivatives as Novel Selective T-Type Ca2+ Channel Blockers", Bioorganic & Medicinal Chemistry Letters 14:3379-3384 (2004).
Mewshaw R.E. et al., "New Generation Dopaminergic Agents. 5. Heterocyclic Bioisosteres that Exploit the 3-OH-N-Phenylpiperazine Dopaminergic Template", Bioorganic & Medicinal Chemistry Letters 8:2675-2680 (1998).

(Continued)

*Primary Examiner* — Patrick T Lewis
(74) *Attorney, Agent, or Firm* — Scully, Scott, Murphy & Presser, P.C.

(57) ABSTRACT

The present invention relates to new morpholinyl anthracycline derivatives which have cytotoxic activity and are useful in treating diseases such as cancer, cellular proliferation disorders and viral infections. The present invention also provides methods for preparing these compounds, pharmaceutical compositions comprising them and methods of treating diseases utilizing such compounds or the pharmaceutical compositions containing them.

11 Claims, No Drawings

(56) References Cited

OTHER PUBLICATIONS

Mishani E. et al., "Formation of Phenylpiperazines by a Novel Alumina Supported Bis-Alkylation", Tetrahedron Letters 37(3):319-322 (1996).
Morrow G.W. et al., "Synthesis of 1-Fluoro-, 4-Fluoro-, and 1,4-Difluoro-4-Demethoxydaunomycinone. Interesting D-Ring Analogues of Adriamycin", The Journal of Organic Chemistry 52(5):719-728 (Mar. 6, 1987).
Ngu K. et al., "Preparation of Acid-Labile Resins With Halide Linkers and Their Utility in Solid Phase Organic Synthesis", Tetrahedron Letters 38(6):973-976 (1997).
Peterson C. et al., "Transport and Storage of Anthracyclines in Experimental Systems and Human Leukemia", Anthracycline Antibiotics in Cancer Therapy, pp. 132-146 (1982).
Rockway T.W. et al., "Inhibitors of HCV NS5B Polymerase: Synthesis and Structure-Activity Relationships of N-1-Benzyl and N-1-[3-Methylbutyl]-4-Hydroxy-1,8-Naphthyridon-3-yl Benzothiadiazine Analogs Containing Substituents on the Aromatic Ring", Bioorganic & Medicinal Chemistry Letters 16:3833-3838 (2006).
Sessa C. et al., "Ongoing Phase I and II Studies of Novel Anthracyclines", Cardiovasc Toxicol 7:75-79 (2007).
Smith T.H. et al., "Synthesis of Daunorubicin Analogues With Novel 9-Acyl Substituents", Journal of Medicinal Chemistry 22(1):40-43 (1979).
Sugimoto K. et al., "Nitrogen-Containing Heterocyclic Compounds Derived from Sparteine I. Synthesis of 5-Oxosparteine", Chem. Pharm. Bull. 14(2):147-151 (1966).
International Search Report dated Aug. 29, 2014 issued in PCT/EP2014/058262.

\* cited by examiner

MORPHOLINYL ANTHRACYCLINE DERIVATIVES

The present invention relates to new morpholinyl anthracycline derivatives, to a process for their preparation, to pharmaceutical compositions containing them and use thereof in the treatment of abnormal cell proliferation diseases. As an example, the compounds of the invention may be used to treat tumors.

Anthracyclines are antibiotic compounds that exhibit cytotoxic activity. Several studies have indicated that anthracyclines may operate to kill cells by a number of different mechanisms including: 1) intercalation with the DNA of a cell thereby inhibiting DNA-dependent nucleic acid synthesis; 2) production of free radicals which then react with cellular macromolecules to cause damage to the cells or 3) interactions with the cell membrane [see, e.g., C. Peterson et al., "Transport and storage of Anthracycline in experimental systems and human leukemia" in Anthracycline Antibiotics In Cancer Therapy (1982), pp. 132-146; and N. R. Bachur, "Free Radical Damage" id. pp. 97-102]. Because of their cytotoxic activity, anthracyclines have been used in the treatment of numerous cancers such as leukemia, breast carcinoma, lung carcinoma, ovarian adenocarcinoma and sarcomas [see e.g., P. H-Wiernik, in Anthracycline: Current Status And New Developments (1980), p 11]. Commonly used anthracyclines include doxorubicin, epirubicin, idarubicin and daunomycin.

In the recent years many new highly cytotoxic anthracycline derivatives have been synthesized.

Anthracycline derivatives bearing a substituted morpholino ring linked at the C-3' position of the sugar moiety have shown promising antitumor activity on experimental murine tumors [see: J. W. Lown, Bioactive Molecules, vol 6, (1988), pp. 55-101] and in clinical trials in the treatment of hepatocellular carcinoma [see: C. Sessa, O. Valota, C. Geroni, *Cardiovascular Toxicology*, vol. 7(2), (2007), pp. 75-79].

New morpholinyl anthracycline derivatives in which the morpholino ring is bridged with an oxygen atom to position C-4' of the sugar residue have been disclosed as antitumor agents in the International Pat. App. WO9802446 in the name of Pharmacia & Upjohn SPA.

4-Amino and 4-fluoro anthracycline derivatives have been also disclosed as antitumor agents in Pat. App. EP 288268 and EP 381989 in the name of Farmitalia Carlo Erba Srl.

Despite the efforts in anticancer research, cancer remains a looming and elusive target, therefore there is still a need for new anticancer agents.

The present invention relates to morpholinyl anthracycline derivatives of formula (I)

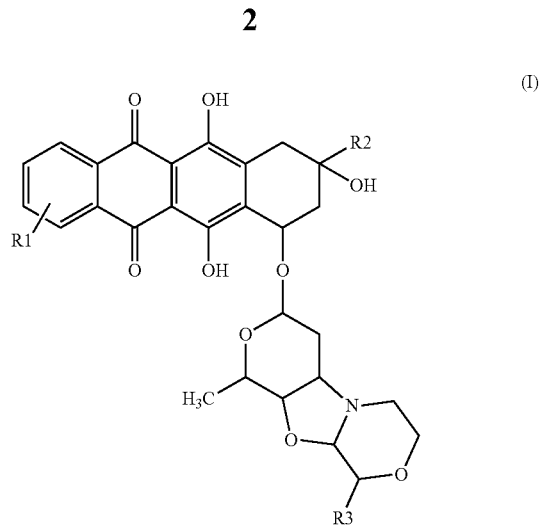

wherein:
R1 is halogen or NR4R5;
R2 is an optionally substituted group selected from straight or branched $C_2$-$C_6$ alkyl, NR7R8-$C_2$-$C_6$ alkyl, R6O—$C_2$-$C_6$ alkyl and COR9;
R3 is hydrogen or a straight or branched $C_1$-$C_4$ alkoxy;
R4 and R5 are independently hydrogen, a monosubstituted-benzyl, a disubstituted-benzyl, or an optionally substituted group selected from straight or branched $C_1$-$C_6$ alkyl, NR7R8-$C_1$-$C_6$ alkyl, R6O—$C_1$-$C_6$ alkyl, R7R8N—$C_1$-$C_6$ alkylcarbonyl, R6O—$C_1$-$C_6$ alkylcarbonyl, R7R8N—$C_1$-$C_6$ alkylaminocarbonyl, R6O—$C_1$-$C_6$ alkylaminocarbonyl, R7R8N—$C_1$-$C_6$ alkylsulphonyl, R6O—$C_1$-$C_6$ alkylsulphonyl, R7R8N—$C_1$-$C_6$ alkoxycarbonyl and R6O—$C_1$-$C_6$ alkoxycarbonyl; or
R4 and R5, taken together with the N atom to which they are bound, form a heterocyclyl substituted with R4;
R6, R7 and R8 are independently hydrogen or an optionally substituted straight or branched $C_1$-$C_6$ alkyl;
R9 is OR6, NR7R8 or an optionally substituted group selected from
straight or branched $C_1$-$C_4$ alkyl, NR7R8-$C_1$-$C_4$ alkyl and R6O—$C_1$-$C_4$ alkyl,
or pharmaceutically acceptable salts.

The present invention also provides methods of synthesizing the morpholinyl anthracycline derivatives of formula (I), prepared through a process consisting of standard synthetic transformations, and their isomers, tautomers, hydrates, solvates, complexes, metabolites, prodrugs, carriers, N-oxides.

Moreover, the present invention provides a pharmaceutical composition comprising a therapeutically effective amount of compounds of formula (I) or a pharmaceutically acceptable salt thereof as defined above and at least one pharmaceutically acceptable excipient, carrier or diluent.

The present invention further provides a pharmaceutical composition comprising a therapeutically effective amount of a compound of formula (I) and one or more chemotherapeutic agents.

The present invention also provides a pharmaceutical composition comprising a therapeutically effective amount of a compound of formula (I) in combination with known anticancer treatments such as radiation therapy or chemotherapy regimen, in combination with cytostatic or cytotoxic agents, antibiotic-type agents, alkylating agents, antimetabolite agents, hormonal agents, immunological agents, interferon-type agents, cyclooxygenase inhibitors (e.g.

COX-2 inhibitors), matrixmetalloprotease inhibitors, telomerase inhibitors, tyrosine kinase inhibitors, anti-growth factor receptor agents, anti-HER2 agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

The present invention also provides a compound of formula (I) as defined above, for use in a method of treating cancer, cellular proliferation disorders and viral infections.

Preferably, a compound of formula (I) as defined above, is for use in a method of treating specific types of cancers, such as but not limited to: carcinomas, including bladder, breast, colon, kidney, liver, lung, comprising small cell lung cancer, esophagus, gall-bladder, ovary, pancreas, stomach, cervix, thyroid, prostate, and skin carcinoma, comprising squamous cell carcinoma; hematopoietic tumors of lymphoid lineage, including leukemia, acute lymphocitic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemia, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannoma; and other tumors, including melanoma, seminoma, teratocarcinoma, osteosarcoma, xeroderma pigmentosum, keratoxanthoma, thyroid follicular cancer, Kaposi's sarcoma and mesothelioma.

Furthermore, a compound of formula (I) as defined above is for use in a method of treating specific cellular proliferation disorders such as, for example, benign prostate hyperplasia, familial adenomatosis polyposis (FAP), neurofibromatosis, psoriasis, vascular smooth cell proliferation associated with atherosclerosis, pulmonary fibrosis, arthritis, glomerulonephritis and post-surgical stenosis and restenosis.

In addition, a compound of formula (I) as defined above is for use in a method of inhibiting tumor angiogenesis and metastasis, as well as in a method of treating organ transplant rejection and host versus graft disease.

The present invention also provides a method for treating cancer, which comprises administering to a mammal in need thereof an effective amount of a compound of formula (I) as defined above. The mammal in need thereof may be for example a human.

Moreover the invention provides the use of a compound of formula (I) or a pharmaceutically acceptable salt thereof, as defined above, in the manufacture of a medicament for treating cancer.

Unless stated otherwise, the following terms and phrases as used herein are intended to have the following meanings.

With the term "straight or branched $C_1$-$C_6$ alkyl" we intend any of the groups such as, for instance, methyl, ethyl, n-propyl, n-butyl, n-pentyl, isopropyl, n-butyl, isobutyl, sec-butyl, tert-butyl.

With the term "straight or branched $C_1$-$C_4$ alkoxy" we intend any of the groups such as, for instance, methoxy, ethoxy, propoxy, etc.

With the term "halogen" we intend a fluorine, chlorine, bromine or iodine.

With the term "monosubstituted-benzyl" we intend any of the groups such as 4-methoxybenzyl, 4-methylbenzyl, 4-fluorobenzyl, 3-methoxybenzyl, 3-methylbenzyl, 3-fluorobenzyl, 2-methoxybenzyl, 2-methylbenzyl, 2-fluorobenzyl, etc.

With the term "disubstituted-benzyl" we intend any of the groups such as 2,4-dimethoxybenzyl, 2,4-dimethylbenzyl, 2,4-difluorobenzyl, 2,3-dimethoxybenzyl, 2,3-dimethylbenzyl, 2,3-difluorobenzyl, 2,5-dimethoxybenzyl, 2,5-dimethylbenzyl, 2,5-difluorobenzyl, 2-fluoro-4-methoxybenzyl, 2-fluoro-4-methylbenzyl, etc.

With the term "straight or branched $C_1$-$C_6$ alkylcarbonyl" we intend any of the groups such as, for instance, methylcarbonyl, ethylcarbonyl, n-butylcarbonyl, isopropylcarbonyl, etc.

With the term "straight or branched $C_1$-$C_6$ alkylaminocarbonyl" we intend any of the groups such as, for instance, methylaminocarbonyl, ethylaminocarbonyl, n-butylaminocarbonyl, isopropylaminocarbonyl, etc.

With the term "straight or branched $C_1$-$C_6$ alkylsulphonyl" we intend any of the groups such as, for instance, methylsulphonyl, ethylsulphonyl, n-butylsulphonyl, isopropylsulphonyl, etc.

With the term "straight or branched $C_1$-$C_6$ alkoxycarbonyl" we intend any of the groups such as, for instance, ethoxycarbonyl, n-butoxycarbonyl, isopropoxycarbony, n-propoxycarbonyl, etc.

The term "heterocyclyl" as used herein refers to a saturated or unsaturated non-aromatic 5- to 7-membered carbocyclic ring, wherein from 1 to 3 carbon atoms are replaced by heteroatoms such as nitrogen, oxygen and sulfur, wherein said heteroatoms may be directly connected to each other, nitrogen and sulfur may optionally be oxidized, nitrogen may optionally be quaternized or bring a R4 substituent. Non limiting examples of heterocyclyl groups are, for instance, piperidinyl, piperazinyl, oxazolidinyl, 4-methylpiperazinyl, 4-ethylpiperazinyl, etc.

The term "aryl" as used herein refers to carbocyclic hydrocarbons with from 1 to 2 ring moieties, either fused or linked to each other by single bonds, wherein at least one of the rings is aromatic. Examples of aryl groups according to the invention are, for instance, phenyl, biphenyl, α- or β-naphthyl, dihydronaphthyl, and the like.

The term "leaving group" refers to a group that can be substituted by another group in a substitution reaction. Such leaving groups are well-known in the art and examples include, but are not limited to, halides (fluoride, chloride, bromide and iodide), azides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, carboxylates, am inocarboxylates (carbamates) and al koxycarboxylates (carbonates). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarbonylate (carbonate) may for example be used as a leaving group. The term "leaving group" also refers to a group that is eliminated as a consequence of an elimination reaction, e.g., an electronic cascade reaction or a spirocyclization reaction. In this instance, an halide, a sulfonate, an azide, an aminocarboxylate (carbamate) or an alkoxycarbonylate (carbonate) may for example be used as a leaving group.

The term "nitrogen protecting group" refers to a group that with the nitrogen atom form carbamates, amides, cyclic imides, N-alkyl and N-aryl amines. Such protecting groups are well-known in the art (see e.g. Green T. W., Wuts P. G. M.; "Protecting groups in organic synthesis"). Non limiting examples of carbamate protecting groups are, for instance, methyl and ethyl carbamate, 9-fluorenylmethyl carbamate (Fmoc), 2,2,2-trichloroethylcarbamate (Troc), t-butyl carbamate (BOC), vinyl carbamate (Voc), allyl carbamate (Alloc), benzyl carbamate (Cbz), p-nitrobenzyl and the like. Non limiting examples of amides are, for instance N-trichloroacetamide, N-trifluoroacetamide (TFA) and the like. Non limiting examples of cyclic imide protecting groups are, for instance, N-phthalimide, N-dithiasuccinoylimide (Dts) and the like. Non limiting examples of N-alkyl and N-aryl protecting groups are, for instance, N-allylamine, N-benzylamine and the like.

The term "hydroxyl protecting group" refers to a group that with the oxygen atom form ethers, esters, cyclic acetals or ketals. Such protecting groups are well-known in the art (see e.g. Green T. W., Wuts P. G. M.; "Protecting groups in organic synthesis"). Non limiting examples of ethers protecting groups are, for instance, alkyl ethers and benzyl ethers, such as methoxymethyl ether (MOM-OR), tetrahydropyranyl ether (THP-OR), allyl ether (Allyl-OR), benzyl ether (Bn-OR), triphenylmethyl ether (Tr-OR) and the like, or silyl ethers, such as trimethylsilyl ether (TMS-OR), t-butyldimethylsilyl ether (TBS-OR or TBDMS-OR), t-butyldiphenylsilyl ether (TBDPS-OR) diphenylmethylsilyl ether (DPMS-OR) and the like. Non limiting examples of esters protecting groups are, for instance, trifluoroacetate, benzoate (Bz-OR) and carbonates, such as ethylcarbonate and the like. Non limiting examples of cyclic acetals or ketals protecting groups are, for instance, methylene acetal, ethylidene acetal, methoxymethylene acetal and the like. The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

With the terms "compounds of formula (Ia)" or "compounds of formula (Ib)" we mean respectively the compounds depicted below:

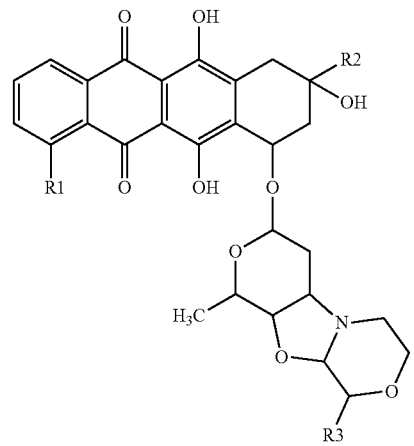

(Ia)

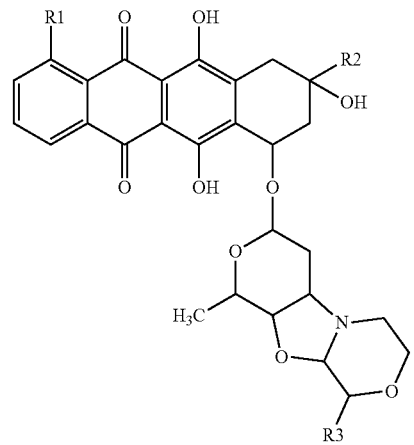

(Ib)

wherein R1, R2 and R3 are as defined above.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

Preferred compounds of formula (I) are the compounds of formula (Ia) or (Ib):

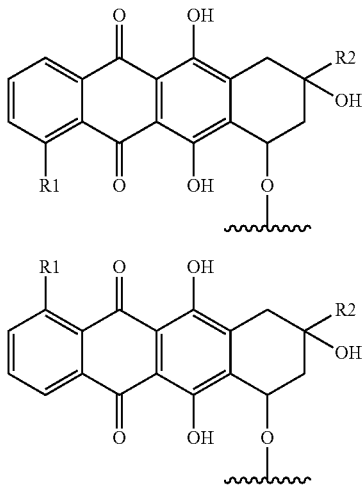

wherein R1 is fluorine or NR4R5, wherein one of R4 or R5 is hydrogen and the other is hydrogen or an optionally substituted group selected from straight or branched $C_1$-$C_6$ alkyl, R7R8N-$C_1$-$C_6$ alkyl, R6O-$C_1$-$C_6$ alkyl, R7R8N-$C_1$-$C_6$ alkylcarbonyl, R6O-$C_1$-$C_6$ alkylcarbonyl, R7R8N-$C_1$-$C_6$ alkylaminocarbonyl, R6O-$C_1$-$C_6$ alkylaminocarbonyl, R7R8N-$C_1$-$C_6$ alkoxycarbonyl and R6O-$C_1$-$C_6$ alkoxycarbonyl.

More preferred compounds of formula (I) are the compounds of formula (Ia):

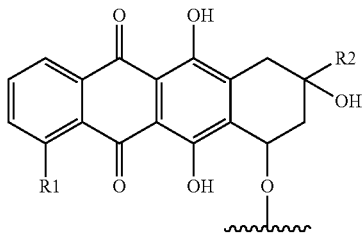

wherein R1 is fluorine or NR4R5 wherein R4 and R5 are as defined above, and
R2 is COR9, wherein R9 is as defined above.

Specific, not limiting, preferred compounds (compd.) of the present invention, optionally in the form of a pharmaceutically acceptable salt, are the following:
1) (8S,10S)-8-acetyl-1-fluoro-6,8,11-trihydroxy-10-{[(1S,3R,4aS,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
2) (8S,10S)-1-fluoro-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
3) (8S,10S)-1-amino-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
4) (8S,10S)-8-acetyl-1-amino-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
5) (8S,10S)-8-acetyl-6,8,11-trihydroxy-1-[(2-hydroxyethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
6) (8S,10S)-6,8,11-trihydroxy-8-(hydroxyacetyl)-1-[(2-hydroxyethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione,
7) (8S,10S)-8-acetyl-1-[(2-aminoethyl)amino]-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, and
8) (8S,10S)-1-[(2-aminoethyl)amino]-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione.

For a reference to any specific compound of formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

A compound of formula (I) is prepared according to any one of the five alternative pathways A to E summarized in Scheme 1 below; also summarized in Scheme 1 is the preparation of the intermediate compound of formula (V) according to Pathway F and the preparation of the starting material compound of formula (II) according to Pathway G.

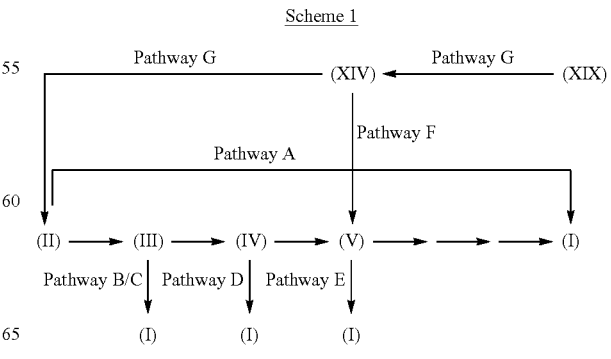

Scheme 1

Pathway A

A compound of formula (I), wherein R1 and R3 are as defined above, and R2 is COR9, wherein R9 is OR6 or NR7R8, wherein R6, R7 and R8 are as defined above, is prepared as summarized in Scheme 2 below.

Scheme 2

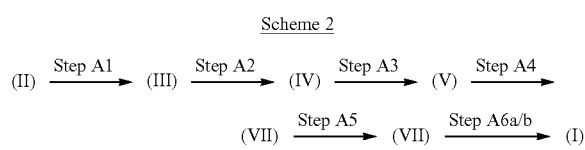

Accordingly, a process of the present invention comprises the following steps:

A1) reacting a compound of formula (II)

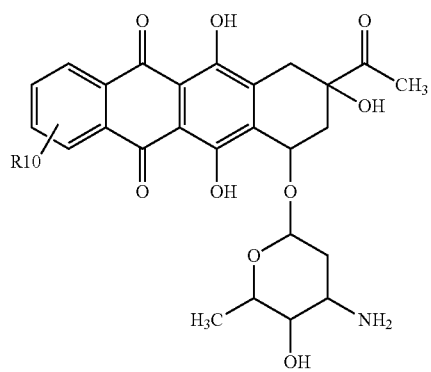

wherein R10 is R1 or a group of formula NR19R20, wherein R19 and R20 are independently a suitable nitrogen protecting group, or one of R19 or R20 is hydrogen and the other is a suitable nitrogen protecting group, and R1 is as defined above,
with a compound of formula (IIa)

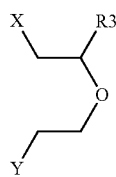

wherein R3 is as defined above and X and Y are, the same or different, a leaving group, preferably halogen;

A2) reacting the resultant compound of formula (III)

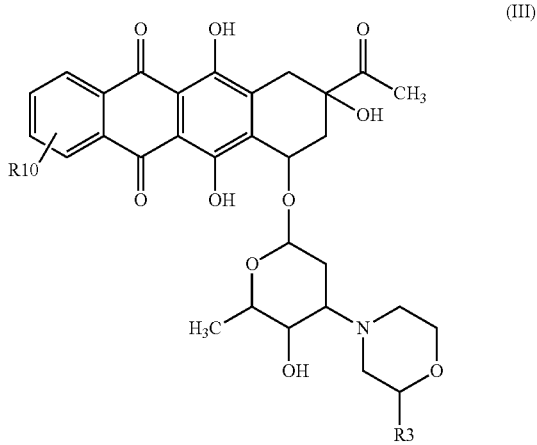

wherein R3 and R10 are as defined above,
with ethylorthoformate and bromine, then adding HBr;

A3) reacting the resultant compound of formula (IV)

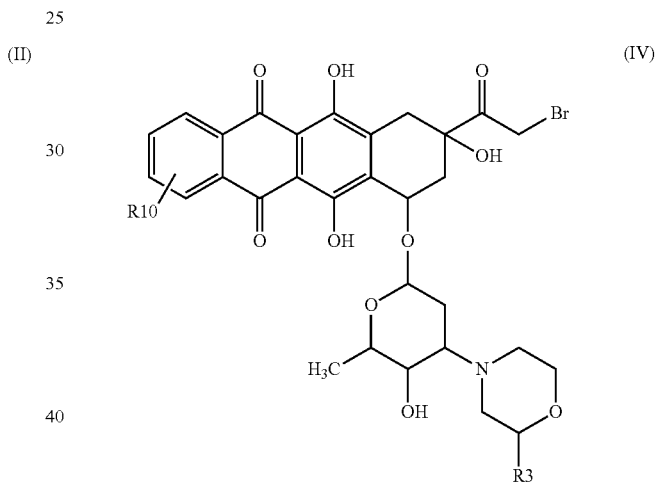

wherein R3 and R10 are as defined above,
with a formylating agent;

A4) oxidizing the resultant compound of formula (V)

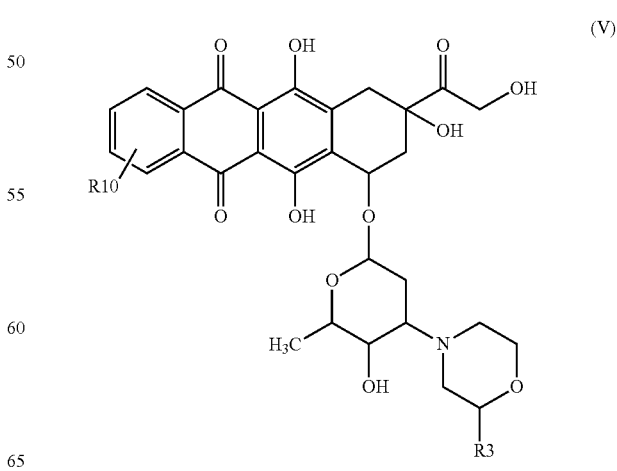

wherein R10 and R3 are as defined above;

A5) reacting the resultant compound of formula (VI)

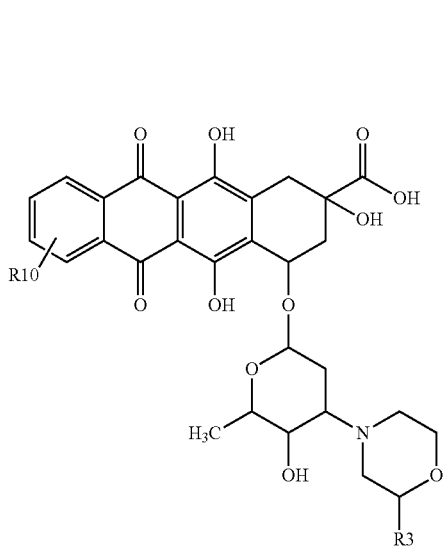

wherein R3 and R10 are as defined above,
with a compound of formula (VIa) or (VIb)

R6-OH         (VIa);

R7R8NH        (VIb)

wherein R6, R7 and R8 are as defined above;
A6a) reacting the resultant compound of formula (VII)

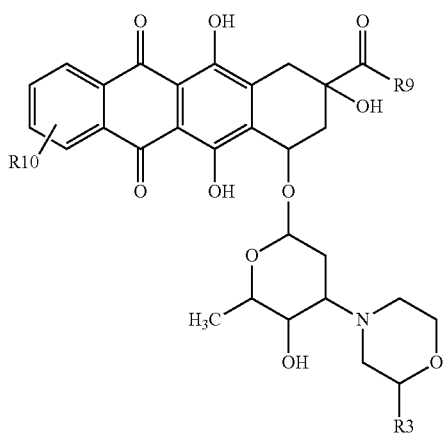

wherein R3, R10 and R9 are as defined above,
first with DMDO;

A6b) then treating the resultant compound of formula (XX)

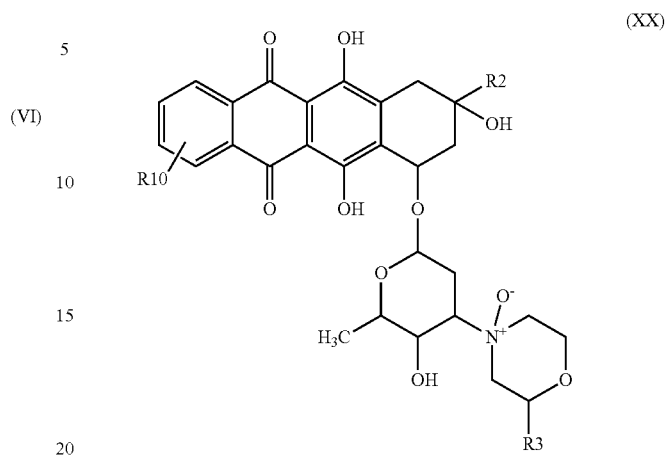

wherein R3 and R10 are as defined above and R2 is COR9, wherein R9 is as defined above, with cyanuric chloride or with an iron (II) salt, and finally, if desired, removing the nitrogen and/or hydroxy protecting group/s to obtain a compound of formula (I)

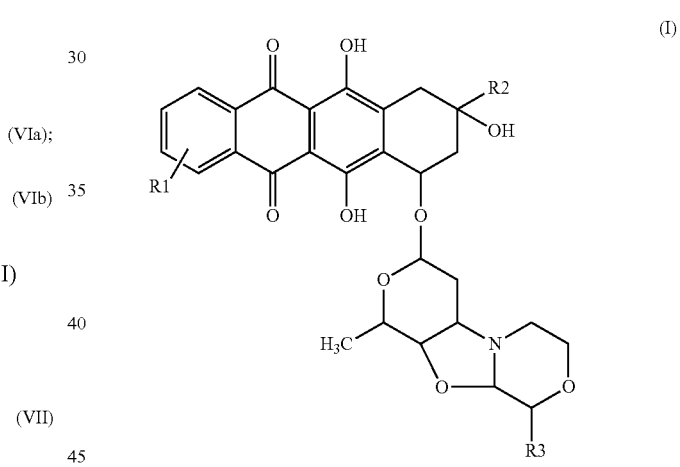

wherein R1 and R3 are as defined above and R2 is COR9, wherein R9 is as defined above;
optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

Pathway B

A compound of formula (I) wherein R1 and R3 are as defined above and R2 is ethyl or COCH₃ is prepared as summarized in Scheme 3 below.

Scheme 3

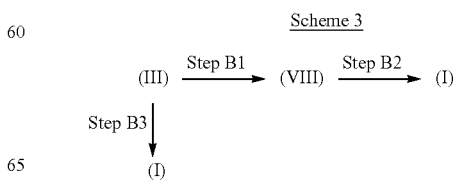

Accordingly, a process of the present invention comprises the following steps:

B1) reacting a compound of formula (III) as defined above, with a hydrazine derivative of formula (IIIa)

(IIIa)

wherein R11 is aryl, preferably phenyl, 4-methylphenyl or 4-halophenyl and then reducing the hydrazide;

B2) reacting the resultant compound of formula (VIII)

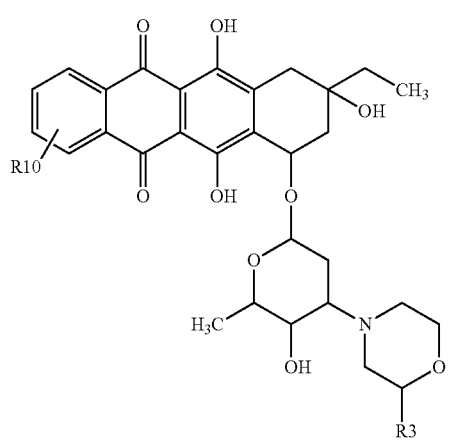
(VIII)

wherein R3 and R10 are as defined above, under the same conditions reported above under steps A6a) and A6b), to obtain a compound of formula (I)

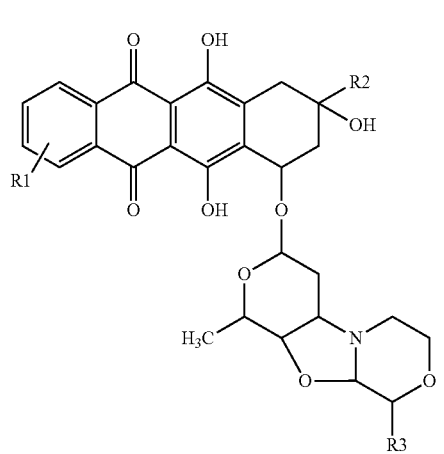
(I)

wherein R1 and R3 are as defined above and R2 is ethyl or

B3) reacting the compound of formula (III) as defined above, under the same conditions reported above under steps A6a) and A6b), to obtain a compound of formula (I)

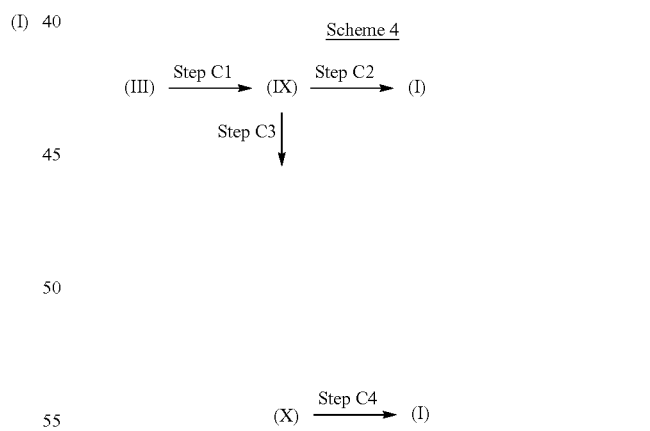
(I)

wherein R1 and R3 are as defined above and R2 is $COCH_3$, optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

Pathway C

A compound of formula (I), wherein R1 and R3 are as defined above and R2 is selected from straight or branched $C_3$-$C_6$ alkyl, NR7R8-$C_3$-$C_6$ alkyl, R6O—$C_3$-$C_6$ alkyl and COR9, wherein R9 is straight or branched $C_2$-$C_4$alkyl, NR7R8-$C_2$-$C_4$ alkyl or R6O—$C_2$-$C_4$ alkyl, wherein R6, R7 and R8 are as defined above, is prepared as summarized in Scheme 4 below.

Scheme 4

(III) $\xrightarrow{\text{Step C1}}$ (IX) $\xrightarrow{\text{Step C2}}$ (I)

Step C3 ↓

(X) $\xrightarrow{\text{Step C4}}$ (I)

Accordingly, a process of the present invention comprises the following steps:

C1) reacting a compound of formula (III), as defined above, with a compound of formula (IIIb)

R12-X  (IIIb)

wherein R12 is a group selected from straight or branched $C_1$-$C_4$ alkyl, NR7R8-$C_1$-$C_4$ alkyl and R6O—$C_1$-$C_4$ alkyl, and X is a leaving group, preferably halogen;

C2) reacting the resultant compound of formula (IX)

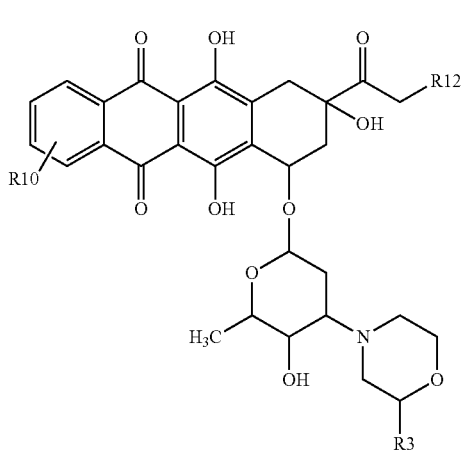

wherein R3, R10 and R12 are as defined above, under the same conditions reported above under steps A6a) and A6b), to obtain a compound of formula (I)

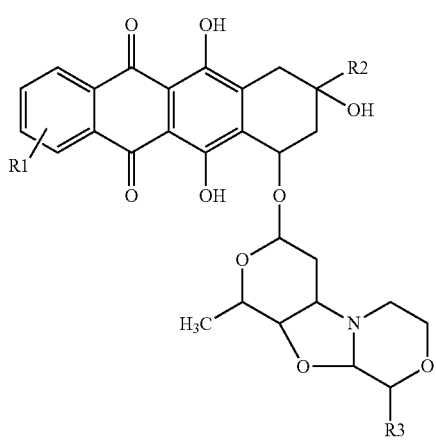

wherein R1 and R3 are as defined above, and R2 is COR9, wherein R9 is straight or branched $C_2$-$C_4$ alkyl, NR7R8-$C_2$-$C_4$alkyl or R6O—$C_2$-$C_4$alkyl, wherein R6, R7 and R8 are as defined above;

or, alternatively,

C3) reacting the compound of formula (IX), as defined above, under the same conditions reported above under step B1;

C4) reacting the resultant compound of formula (X)

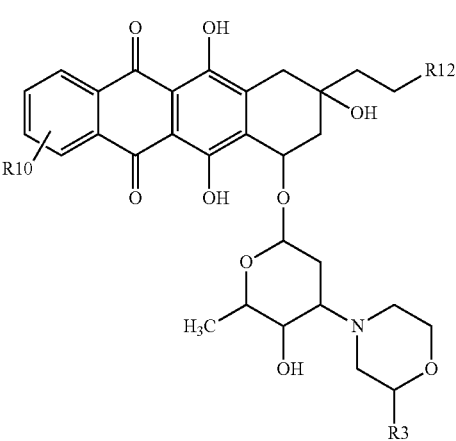

wherein R3, R10 and R12 are as defined above, under the same conditions reported above under steps A6a) and A6b), to obtain a compound of formula (I)

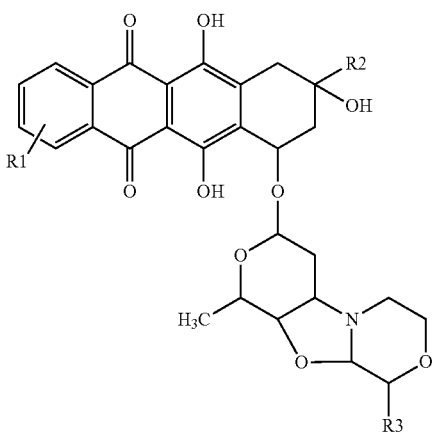

wherein R1 and R3 are as defined above, and R2 is a group selected from straight or branched $C_3$-$C_6$ alkyl, NR7R8-$C_3$-$C_6$ alkyl and R6O—$C_3$-$C_6$ alkyl, wherein R6, R7 and R8 are as defined above;

optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

Pathway D

A compound of formula (I) wherein R1 and R3 are as defined above and R2 is $CH_2$—$CH_2NR7R8$, $CH_2$—$CH_2OR6$ or COR9, wherein R9 is —$CH_2NR7R8$ or —$CH_2OR6$, wherein R6, R7 and R8 are as defined above, is prepared as summarized in Scheme 5 below.

Scheme 5

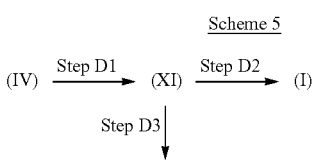

-continued (XII) →(Step D4)→ (I)

Accordingly, a process of the present invention comprises the following steps:

D1) reacting the compound of formula (IV) as defined above, wherein the carbonyl function can be optionally activated as phenylhydrazone derivative, with a compound of formula (IVa) or (IVb)

HN—R7R8 (IVa),

HOR6 (IVb)

wherein R6, R7 and R8 are as defined above and wherein the OH group can be optionally activated as e.g tosyl or mesyl derivative and then, if present, removing the hydrazone function by hydrolysis;

D2) reacting the resultant compound of formula (XI) or (XIa)

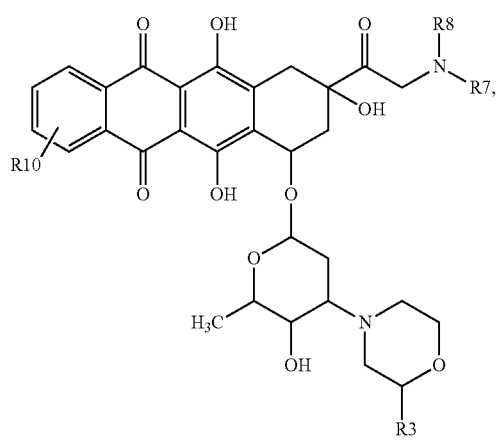

(XI)

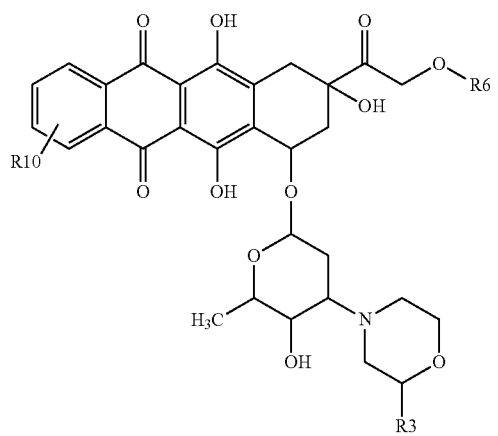

(XIa)

wherein R3, R6, R7, R8 and R10 are as defined above, under the same conditions reported above under steps A6a) and A6b), to obtain a compound of formula (I)

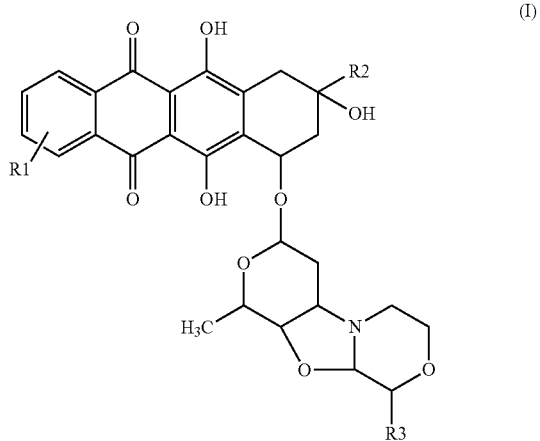

(I)

wherein R1 and R3 are as defined above and R2 is COR9, wherein R9 is a —CH$_2$—NR7R8 or —CH$_2$—OR6, wherein R6, R7 and R8 are as defined above;

or, alternatively,

D3) reacting the resultant compound of formula (XI) or (XIa), as defined above, under the same conditions reported above under step B1, D4) reacting the resultant compound of formula (XII) or (XIIa)

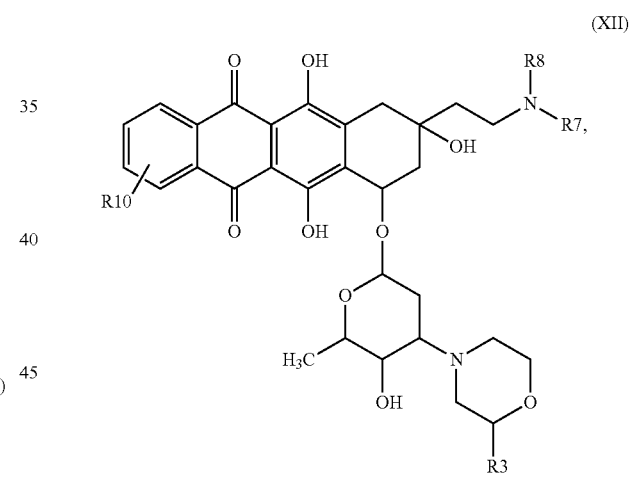

(XII)

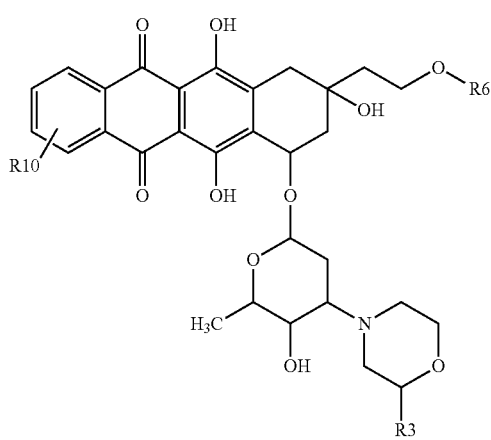

(XIIa)

wherein R3, R6, R7, R8 and R10 are as defined above, under the same conditions reported above under steps A6a) and A6b), to obtain a compound of formula (I)

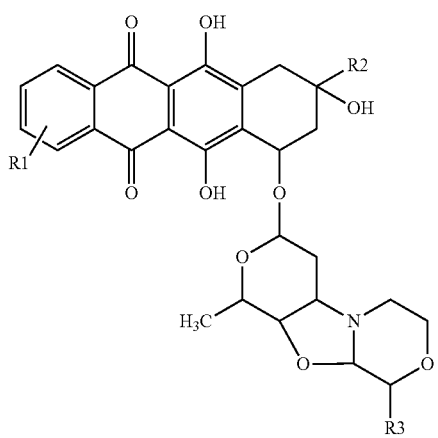

wherein R1 and R3 are as defined above and R2 is —CH$_2$—CH$_2$—NR7R8 or —CH$_2$—CH$_2$—OR6, wherein R6, R7 and R8 are as defined above;

optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

Pathway E

A compound of formula (I) wherein R1 and R3 are as defined above and R2 is CH$_2$OH or COR9, wherein R9 is CH$_2$OH, is prepared as summarized in Scheme 6 below.

Scheme 6

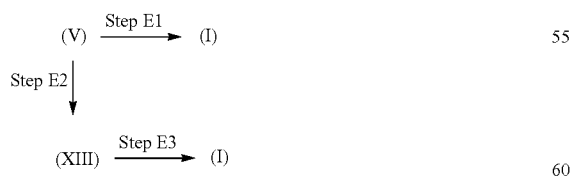

Accordingly, a process of the present invention comprises the following steps:

E1) reacting a compound of formula (V) as defined above, under the same conditions reported above under the steps A6a) and A6b), to obtain a compound of formula (I)

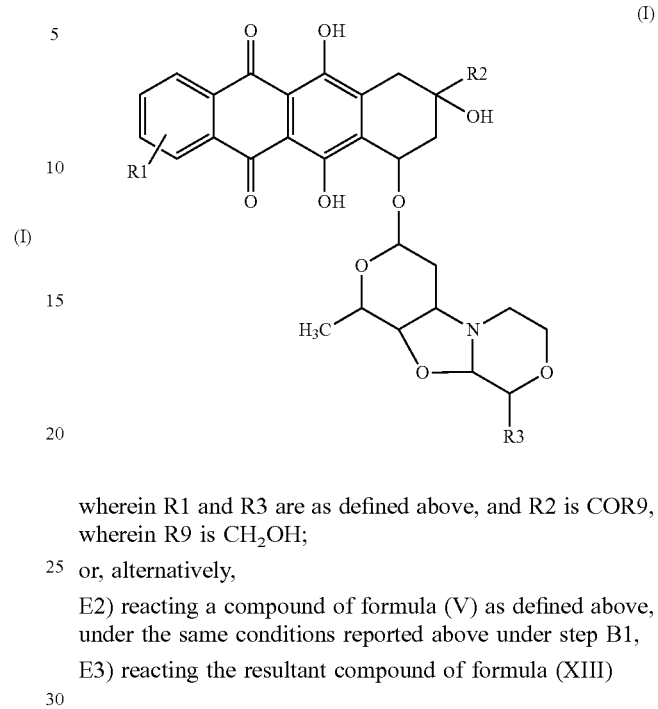

wherein R1 and R3 are as defined above, and R2 is COR9, wherein R9 is CH$_2$OH;

or, alternatively,

E2) reacting a compound of formula (V) as defined above, under the same conditions reported above under step B1, E3) reacting the resultant compound of formula (XIII)

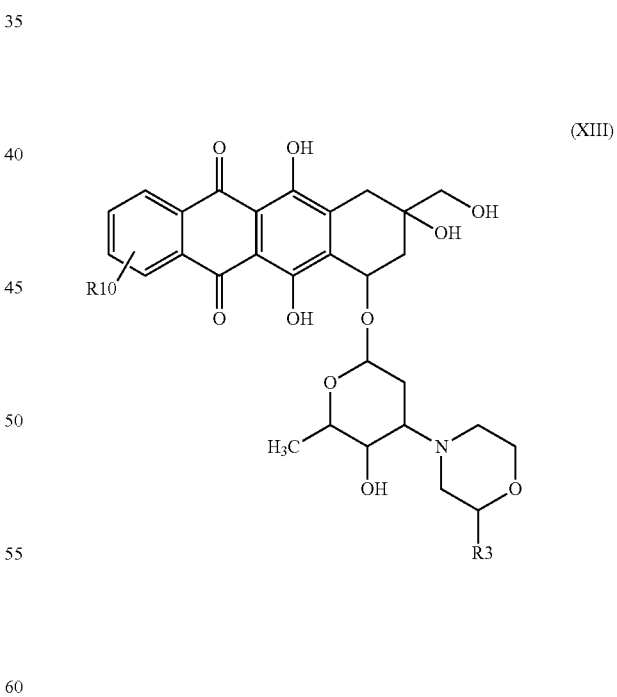

wherein R10 and R3 are as defined above, under the same conditions reported above under steps A6a) and A6b), to obtain a compound of formula (I)

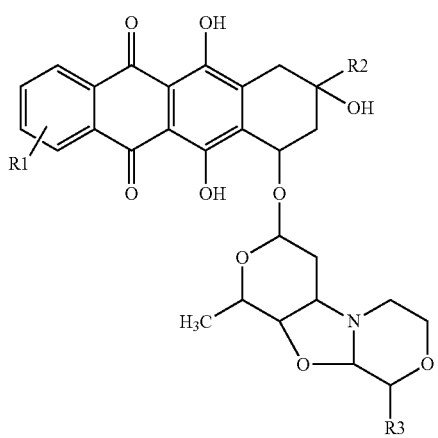

(I)

wherein R1, R3 are as defined above and R2 is CH$_2$OH; optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

According to step A1) the reaction of the compound of formula (II) with the compound of formula (IIa) is performed in an organic solvent, preferably DMF, at room temperature, following well known procedures reported in the art (see for example WO91/09046).

According to step A2) the reaction of the compound of formula (III) with ethylorthoformate and bromine and then with HBr is performed in two steps following well known procedures reported in the art (see for example Doxorubicin Anticancer Antibiotics Vol. 17, 1981, p. 168; F. Arcamone et al. J. Med. Chem. 1974, 17, p. 335).

According to step A3) the reaction to obtain the compound of formula (V) is performed following well known procedures reported in the art (see for example Doxorubicin Anticancer Antibiotics Vol. 17, 1981, p. 168; U.S. Pat. No. 3,803,124). An example that is not intended to limit the method is the reaction of the compound of formula (IV) with sodium formate. The reaction is performed in CH$_3$CN or acetone or a mixture of them, at a temperature ranging from about 20° C. to reflux and for a time ranging from about 30 minutes to about 24 hours.

According to step A4) the oxidation of the compound of formula (V) is performed with an oxidizing reagent, preferably NaIO$_4$. The reaction is performed in MeOH or water or a mixture of them, at a temperature ranging from about 20° C. to reflux and for a time ranging from about 30 minutes to about 24 hours.

According to step A5) the coupling reaction between the compound of formula (VI) and the compound of formula (VIa) or (VIb) is performed following well known procedures reported in the art (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio, 2010). An example that is not intended to limit the method is the reaction of the compound of formula (VI) with a compound of formula (VIa) in presence of a condensing agent such as for example DCC or EDC. The reaction is carried out in an organic solvent, preferably DMF, at a temperature ranging from about 20° C. to reflux and for a time ranging from about 30 minutes to about 24 hours.

According to steps A6a) and 6Ab) the reaction of the compound of formula (VII) first with DMDO and then the reaction of the resultant compound of formula (XX) with cyanuric chloride or with an iron (II) salt is carried out following well known procedures reported in the art (see e.g. GB2296495A; WO2012073217; WO9802446).

Removal of the nitrogen and/or hydroxy protecting groups, if necessary, is performed following well known procedures reported in the art (see e.g. Protective Groups in Organic Synthesis; Theodora W. Greeen, Peter G. M. Wuts 4$^{th}$ edition).

According to step B1) the reaction of the compound of formula (III) with the compound of formula (IIIa) is carried out in an organic solvent, preferably MeOH, at a temperature ranging from about −10° C. to about 50° C. and for a time ranging from about 30 minutes to about 96 hours. Subsequent reduction of the hydrazide derivative to obtain the compound of formula (VIII) is carried out with NaBH$_4$ or NaBH$_3$CN in presence of camphorsulfonic acid. The reaction is carried out in an organic solvent, preferably MeOH, at a temperature ranging from about 20° C. to reflux and for a time ranging from about 30 minutes to about 5 hours (see also Doxorubicin Anticancer Antibiotics Vol. 17, 1981, p. 165).

According to step B2 and B3) the reaction is respectively carried out as described above under steps A6a) and A6b).

According to step C$_1$) the reaction of the compound of formula (III) with the compound of formula (IIIb) is carried out in an organic solvent, preferably DMF following well known procedures reported in the art (see e.g. Smith T. H., Fujiwara A. N., Henry D. W.; J. Med. Chem. 1979, 22, p. 40).

According to step C$_2$) the reaction of the compound of formula (IX) is carried out as described above under steps A6a) and A6b).

According to step C3) the reaction of the compound of formula (IX) is carried out as described above under step B1.

According to step C4) the reaction of the compound of formula (X) is carried out as described above under steps A6a) and A6b).

According to step D1) the reaction of the compound of formula (IV) with the compound of formula (IVa) or (IVb) is optionally performed in the presence of a base, preferably diethylamine. The reaction is carried out in an organic solvent, preferably acetone at a temperature ranging from about 20° C. to reflux and for a time ranging from about 30 minutes to about 24 hours (see U.S. Pat. No. 4,133,877).

Removal of hydrazone function can be carried out under hydrolitic conditions as reported in Baker, T. S.; Exley, D.; Steroids 1977, 29, p. 429; Sugimoto, K.; Sunakawa, N.; Ohki, S.; Chem Pharm Bull 1966, 14, p. 147.

According to step D2) the reaction of the compound of formula (XI) or (XIa) is carried out as described above under steps A6a) and A6b).

According to step D3) the reaction of the compound of formula (XI) or (XIa) is carried out as described above under step B1.

According to step D4) the reaction of the compound of formula (XII) or (XIIa) is carried out as described above under steps A6a) and A6b).

According to step E1) the reaction of the compound of formula (V) is carried out as described above under steps A6a) and A6b).

According to step E2) the reaction of the compound of formula (V) is carried out as described above under step B1.

According to step E3) the reaction of the compound of formula (XIII) is carried out as described above steps A6a) and A6b).

Pathway F

The intermediate compound of formula (V) as defined above is alternatively prepared according to Scheme 7 below.

Scheme 7

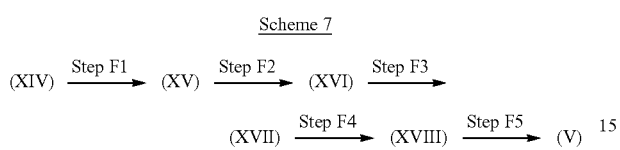

Accordingly, a process of the present invention comprises the following steps:

F1) reacting a compound of formula (XIV)

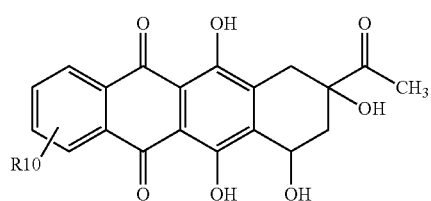

wherein R10 is as defined above, with bromine and potassium acetate;

F2) reacting the resultant compound of formula (XV)

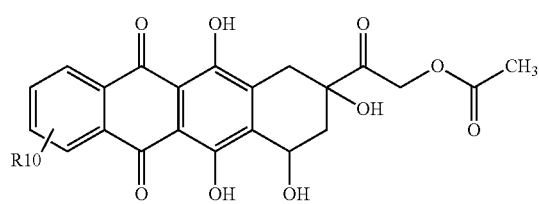

wherein R10 is as defined above, with the sugar of formula (XVa)

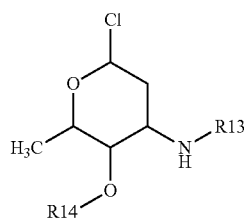

wherein R13 and R14 are independently hydrogen or a suitable nitrogen and/or hydroxy protecting group as e.g. trifluoroacetyl or benzyl;

F3) reacting the resultant compound of formula (XVI)

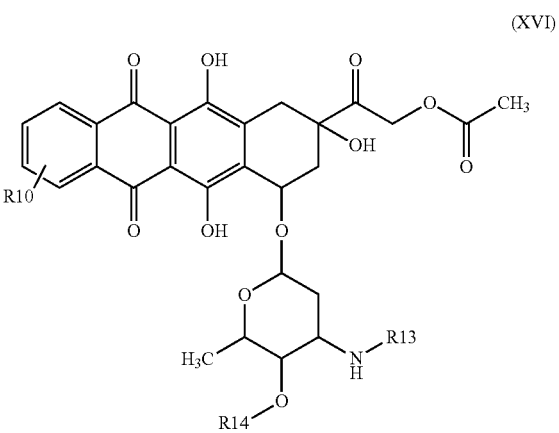

wherein R10, R13 and R14 are as defined above, with ethylorthoformate and pyridinium p-toluenesulfonate (PPTS);

F4) reacting the resultant compound of formula (XVII)

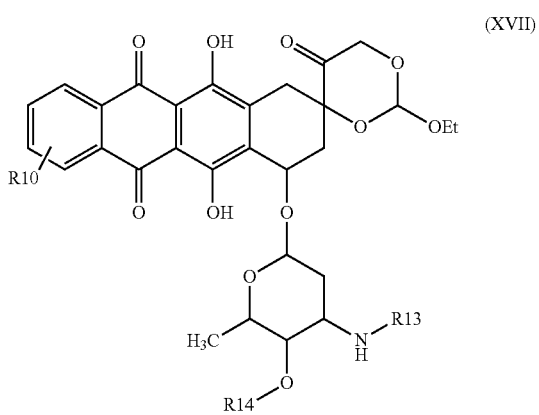

wherein R13 is hydrogen and R10 and R14 are as defined above, with a compound of formula (IIa) as defined above;

F5) deprotecting the resultant compound of formula (XVIII)

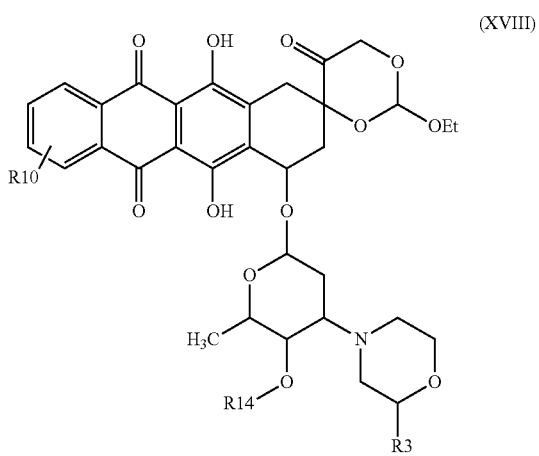

wherein R3, R10 and R14 are as defined above, to yield the compound of formula (V) as defined above.

According to step F1) the reaction is performed in an organic solvent preferably acetone or dioxane, at a temperature ranging from 20° C. to reflux and for a time ranging from about 30 minutes to about 24 hours.

According to step F2) the glicosidation reaction of the compound of formula (XV) is performed in presence of silver trifluoromethanesulfonate following well known procedures reported in the art (see for example GB2225781; GB2215332A).

According to step F3) the reaction to obtain the compound of formula (XVII) is performed reacting the compound of formula (XVI) with ethylorthoformate and PPTS. The reaction is performed in an organic solvent, preferably DCM, at a temperature ranging from 0° C. to reflux and for a time ranging from about 30 minutes to about 24 hours.

According to step F4) the reaction is performed as described above under step A1.

According to step F5) the removal of the hydroxy protecting group is performed following well known procedures reported in the art (see e.g. Protective Groups in Organic Synthesis; Theodora W. Greeen, Peter G. M. Wuts $4^{th}$ edition).

Pathway G

A compound of formula (II) as defined above, wherein R10 is as defined above, except $NH_2$ and halogen, is prepared according to Scheme 8 described below.

Scheme 8

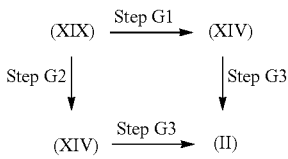

Accordingly, a process of the present invention comprises the following steps:
either
G1) reacting a compound of formula (XIX)

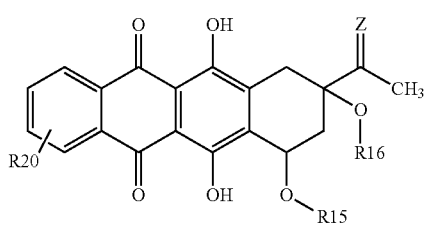

wherein R15 and R16 are independently hydrogen or a suitable hydroxy protecting group, such as e.g trifluoroacetyl, 9-fluorenylmethyl, di-t-butylmethylsilyl, t-butyldiphenylsilyl, or diphenylmethylsilyl, R20 is R10 wherein R10 is NH—R19, wherein R19 is independently hydrogen or a suitable nitrogen protecting group, and Z is oxygen or a suitable carbonyl protecting group, such as an acetal or ketal, preferably, 1-3-dioxane or 1-3-dioxolane,
either
i) with a compound of formula (XIXa), (XIXb), (XIXc) or (XIXd)

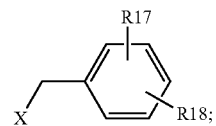

(XIXa)

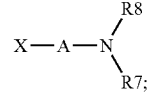

(XIXb)

(XIXc)

(XIXd)

wherein X is a leaving group, preferably halogen; R17 and R18, the same or different, are independently hydrogen, halogen, straight or branched $C_1$-$C_3$ alkyl or $C_1$-$C_3$ alkoxy; A is straight or branched $C_1$-$C_6$ alkyl; and R6, R7 and R8 are as defined above, to obtain, after removal of the protecting groups, if present, the corresponding compound of formula (XIV), as defined above, wherein R10 is a group R1 of formula NR4R5 wherein R4 and R5 are independently hydrogen, a monosubstituted-benzyl, a disubstituted-benzyl, or an optionally substituted group selected from straight or branched $C_1$-$C_6$ alkyl, NR7R8-$C_1$-$C_6$ alkyl and R6O—$C_1$-$C_6$ alkyl, but not both hydrogen;
or
ii) with a compound of formula (XIXe) or (XIXf)

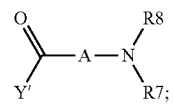

(XIXe)

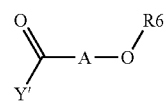

(XIXf)

wherein Y' is OH or a leaving group, preferably chlorine and A, R6, R7 and R8 are as defined above, to obtain, after removal of the protecting groups, if present, the corresponding compound of formula (XIV), as defined above, wherein R10 is a group R1 of formula NR4R5 wherein one of R4 or R5 is hydrogen and the other is a group R7R8N—$C_1$-$C_6$ alkylcarbonyl or R6O—$C_1$-$C_6$ alkylcarbonyl;
or
iii) with a compound of formula (XIXg) or (XIXh)

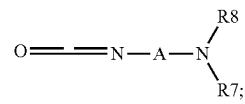

(XIXg)

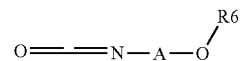

(XIXh)

wherein A, R6, R7 and R8 are as defined above to obtain, after removal of the protecting groups, if present, the corresponding compound of formula (XIV), as defined above, wherein R10 is a group R1 of formula NR4R5 wherein one of R4 or R5 is hydrogen and the other is a group R7R8N—$C_1$-$C_6$ alkylaminocarbonyl or R6O—$C_1$-$C_6$ alkylaminocarbonyl;

or iv) with a compound of formula (XIXi) or (XIXm)

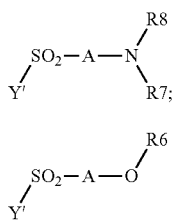

(XIXi)

(XIXm)

wherein Y is OH or a leaving group, preferably chlorine and A, R6, R7 and R8 are as defined above, to obtain, after removal of the protecting groups, if present, the corresponding compound of formula (XIV), as defined above, wherein R10 is a group R1 of formula NR4R5 wherein one of R4 or R5 is hydrogen and the other is a group R7R8N—$C_1$-$C_6$ alkylsulphonyl or R6O—$C_1$-$C_6$ alkylsulphonyl;

or v) with a compound of formula (XIXn) or (XIXo)

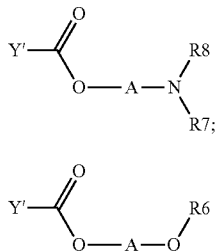

(XIXn)

(XIXo)

wherein Y', A, R6, R7 and R8 are as defined above, to obtain, after removal of the protecting groups, if present, the corresponding compound of formula (XIV), as defined above, wherein R10 is a group R1 of formula NR4R5 wherein one of R4 or R5 is hydrogen and the other is a group R7R8N—$C_1$-$C_6$ alkoxycarbonyl or R6O—$C_1$-$C_6$ alkoxycarbonyl;

or vi) with a compound of formula (XIXp)

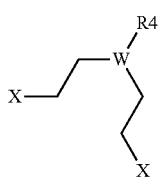

(XIXp)

wherein W is CH or N, and R4 and X are as defined above, to obtain, after removal of the protecting groups, if present, the compound of formula (XIV), as defined above, wherein R10 is a group R1 of formula NR4R5, wherein R4 and R5 taken together with the N atom to which they are bound, form a 6-membered heterocyclyl substituted with R4;

or,

G2) reacting a compound of formula (XIX)

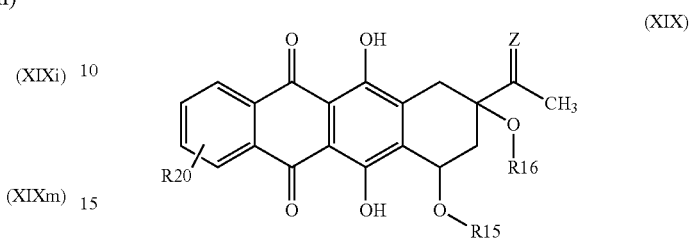

(XIX)

wherein R15, R16 and Z are as defined above and R20 is a suitable leaving group, as, for instance, mesylate, tosylate or 4-fluoro-benzenesulfonate, with a compound of formula (XIXq)

(XIXq)

wherein R4 and R5 are independently hydrogen, a mono-substituted-benzyl, a disubstituted-benzyl, or an optionally substituted group selected from straight or branched $C_1$-$C_6$ alkyl, NR7R8-$C_1$-$C_6$ alkyl and R6O—$C_1$-$C_6$ alkyl; or, R4 and R5, taken together with the N atom to which they are bound, form a substituted heterocyclyl;

to obtain, after removal of the protecting groups, if present, the corresponding compound of formula (XIV), as defined above, wherein R10 is a group R1 of formula NR4R5, wherein R4 or R5 are as defined above;

G3) reacting the resultant compound of formula (XIV)

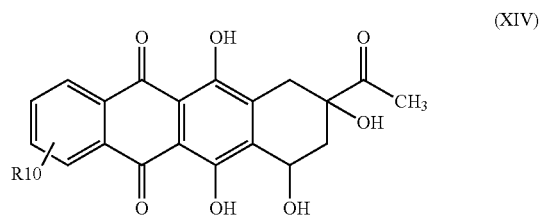

(XIV)

wherein R10 is as defined under steps G1 or G2,
with a compound of formula (XVa) as defined above, under the same conditions reported above under the step F2, to obtain the compound of formula (II) wherein R10 is as defined above.

According to step G1 i) the reaction is performed following well known procedures reported in the art (see for example Ngu, K.; Patel, D. V. Tetrahedron Lett 1997, 38 (6), pp. 973-976). As example, that is not intended to limit the method, the reaction is carried out in DCM, at a temperature ranging from 20° C. to reflux and for a time ranging from 30 minutes to about 24 hours.

According to step G1ii) the coupling reaction between the compound of formula (XIX) and the compound of formula (XIXe) or (XIXf) is performed following well known procedures reported in the art (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio, 2010). An example, that is not intended to limit the method, is the reaction in presence of a condensing agent such as for example DCC, EDC sodium formate. The reaction is carried out in an organic solvent, preferably DMF, at a temperature ranging from 20° C. to reflux and for a time ranging from 30 minutes to about 24 hours.

According to step G1 iii) the reaction is performed following well known procedures reported in the art (see for example Gopalsamy A.; et al. Bioorg Med Chem Lett 2005, 15 (6), pp. 1591-1594; Lee Y. S. et al. Bioorg Med Chem Lett 2004, 3 14, (13), pp. 3379-3384). As example, that is not intended to limit the method, the reaction is carried out in pyridine, DCM, at a temperature ranging from 20° C. to reflux and for a time ranging from 30 minutes to about 24 hours.

According to step G1 iv) the reaction is performed following well known procedures reported in the art (see for example Filimonov S. J Heterocycl Chem 2006, 43, pp. 663-671; Rockway, T. W.; et al.; Bioorg Med Chem Lett 2006, 16, p. 3833).

According to step G1v) the reaction is performed following well known procedures reported in the art (see for example Fukuoka S. et al. J. Chem. Soc. Chem. Commun. 1984, 6, p. 399).

According to step G1vi) the reaction is performed following well known procedures reported in the art (see for example Ismailov, V. et al.; Russ J Org Chem, 2004, 40 (2), pp. 284-285; Mewshaw R. E.; et al.; Bioorg Med Chem Lett 1998, 8 (19), pp. 2675-2680; Mishani E. et al.; Tetrahedron Lett 1996, 37 (3), pp. 319-322. As example, that is not intended to limit the method, the reaction is carried out in DMSO, DCM, MeOH or a mixture of them, optionally in presence of a base or lewis acid (e.g. $Al_2Cl_3$) at a temperature ranging from 20° C. to reflux and for a time ranging from 30 minutes to about 24 hours.

According to step G2) the reaction is carried out as described in Pat. App. GB2215322. As example, that is not intended to limit the method, the reaction is carried out in $CH_3CN$, THF or DMF, optionally in presence of a base at a temperature ranging from 20° C. to reflux and for a time ranging from 1 to 72 hours. According to step G3) the reaction is carried out as described above under the step F2.

The compounds of formula (II) wherein R10 is $NH_2$ can be prepared as described in Pat. App. EP288268.

The compounds of formula (II) wherein R10 is halogen can be prepared as described in Pat. App. WO9802446; and in Gary W et al. J.O.C 1987, 52, p. 713.

The compounds of formula (XIX) can be prepared as described in Pat. App. EP288268.

The compounds of the formula (IIa), (IIIa), (IIIb), (IVa), (IVb), (XVa), (XiXa) to (XIXp) are either commercially available or can be prepared with known methods.

From all of the above, it is clear to the skilled person that when preparing the compounds of formula (I) according to any one of the aforementioned process variants, optional functional groups within the starting materials or the intermediates thereof, that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I) is within the scope of the present invention.

Pharmacology

The new morpholinyl anthracycline derivatives of the present invention are useful as antitumor agents.

A mammal, e.g. a human or animal, may therefore be treated by a method comprising administering thereto a pharmaceutically effective amount of a morpholinyl anthracycline derivative of formula (I).

The condition of the human or animal may be ameliorated or improved in this way.

The evaluation of the cytotoxicity of the compounds of formula (I) is assessed as described below.

In Vitro Cell Proliferation Assay

Human cancer cell lines were seeded in white 384 well-plates (1250 cells/well) in complete medium (RPMI1640 or E-MEM plus 10% Fetal bovine serum) and treated with compounds dissolved in 0.1% DMSO, 24 h after seeding. The cells were incubated at 37° C. and 5% $CO_2$ and after 72 h the plates were processed using CellTiter-Glo assay (Promega) following the manufacturer's instruction.

CellTiter-Glo is a homogenous method based on the quantification of the ATP present, an indicator of metabolically active cells. ATP is quantified using a system based on luciferase and D-luciferin resulting into light generation.

Briefly, 25 μL/well of reagent solution are added to each well and after 5 minutes shaking microplates are read by a luminometer. The luminescent signal is proportional to the number of live cells present in culture.

Dose-response curves were generated by sigmoid function interpolation of 8 concentration points and the antiproliferative activity of compounds was reported as the half-maximal inhibitory concentration ($IC_{50}$).

Representative compounds of the invention of formula (I) were tested in the specific in vitro cell proliferation assay described above.

| | Cell Line $IC_{50}$ nM | | | | | | |
|---|---|---|---|---|---|---|---|
| Cell Line | A2780 | HCC1954 | HCT-116 | HELA | MCF7 | MDA-MB_213 | MDA-MB-468 |
| Compd. 1 | 0.032 | 0.377 | 0.146 | 0.349 | 3.52 | 0.306 | 0.072 |
| Compd. 4 | 0.044 | 0.549 | 0.2 | 0.7 | 0.668 | 0.538 | 0.313 |

As can be appreciated by the skilled person, all these representative compounds are thus particularly advantageous in antitumor therapy.

The compounds of the present invention can be administered either as single agents or, alternatively, in combination with known anticancer treatments such as radiation therapy or chemotherapy regimen, in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, the weight, the conditions of the patient and the administration route.

For example, a suitable dosage adopted for oral administration of a compound of formula (I) may range from about 1 to about 300 mg per dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. subcutaneously, intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, for instance, syrups, emulsions and suspensions. As an example, the syrups may contain, as carrier, saccharose or saccharose with glycerine and/or mannitol and sorbitol. The suspensions and the emulsions may contain, as examples of carriers, natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples. The compounds of the present invention, as prepared according to the following examples, were also characterized by $^1$H-NMR and/or by Exact mass data ESI(+).

$^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N-$^{31}$P}).

Chemical shifts were referenced with respect to the residual solvent signals (DMSO-$d_6$: 2.50 ppm for $^1$H, where not otherwise specified). Data are reported as follows: chemical shift (δ), multiplicity (s=singlet, d=doublet, t=triplet, q=quartet, br. s.=broad singlet, td=triplet of doublets, dd=doublet of doublets, ddd=doublet of doublets of doublets, m=multiplet, spt=septet), coupling constants (J, Hz), and number of protons.

Exact mass data ESI(+) were obtained on a Waters Q-Tof Ultima mass spectrometer directly connected with a Agilent 1100 micro-HPLC system as previously described (M. Colombo, F. Riccardi-Sirtori, V. Rizzo, *Rapid Commun. Mass Spectrom.* 2004, 18, 511-517).

The examples below as well as throughout the application, the following abbreviations have the following meanings. If not defined, the terms have their generally accepted meanings.

| ABBREVIATIONS | |
|---|---|
| DCC | N,N'-dicyclohexylcarbodiimide |
| DCM | dichloromethane |
| DIPEA | N,N-diisopropylethylamine |
| DMDO | dimethyldioxirane |
| DMF | N,N-dimethylformamide |
| DMSO | dimethyl sulfoxide |
| EDCI | N-ethyl-N',N'-diisopropylcarbodiimide hydrochloride |
| EDC | 1-ethyl-3-(3-dimethylaminopropyl)carbodiimide |
| Et$_2$O | diethyl ether |
| EtOAc | ethyl acetate |
| EtOH | ethanol |
| HCl | hydrochloric acid |
| HOBt | 1H-benzotriazol-1-ol |
| MeOH | methanol |
| Na$_2$SO$_4$ | sodium sulfate |
| NaHCO$_3$ | sodium hydrogen carbonate |
| NaOH | sodium hydroxide |
| PPTS | pyridinium p-toluenesulfonate |
| TEA | triethylamine |
| TFA | trifluoro acetic acid |
| THF | tetrahydrofurane |

Example 1

Step A1, Step B3 (according to A6a and A6b)

(8S,10S)-8-acetyl-1-fluoro-6,8,11-trihydroxy-10-{[(1S,3R,4aS,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 1) [R1=F, R2=CH₃CO—, R3=CH₃O—]

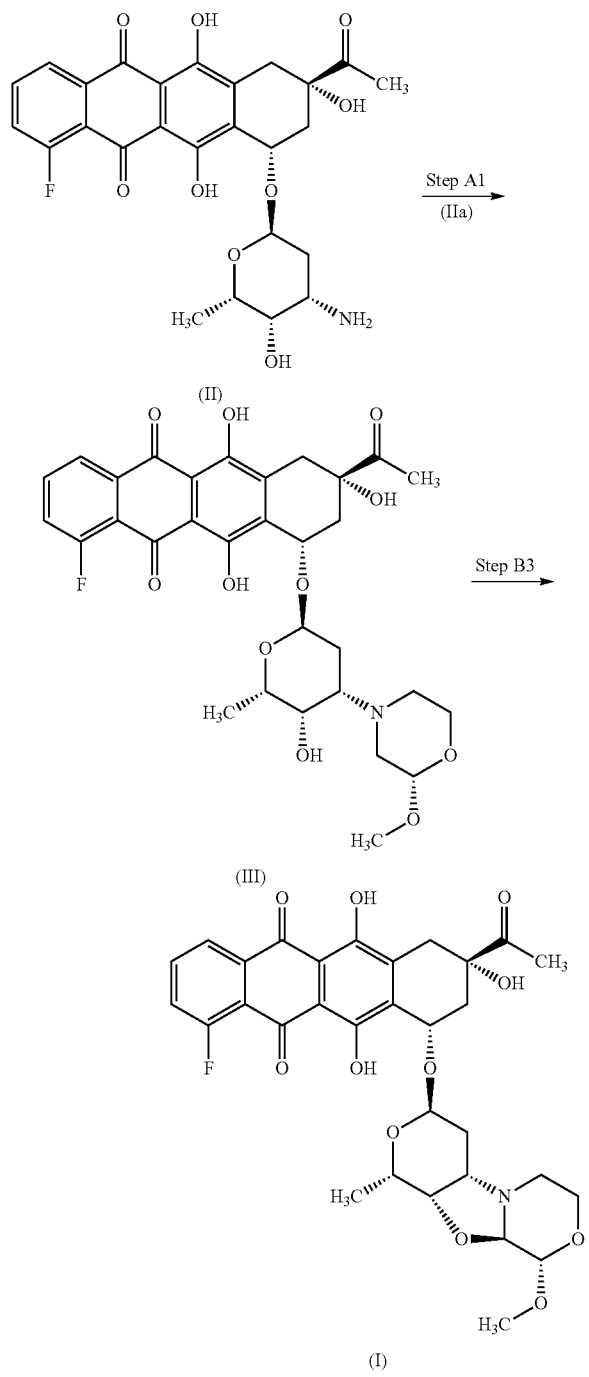

Step A1

(1S,3S)-3-acetyl-10-fluoro-3,5,12-trihydroxy-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside [(III)]

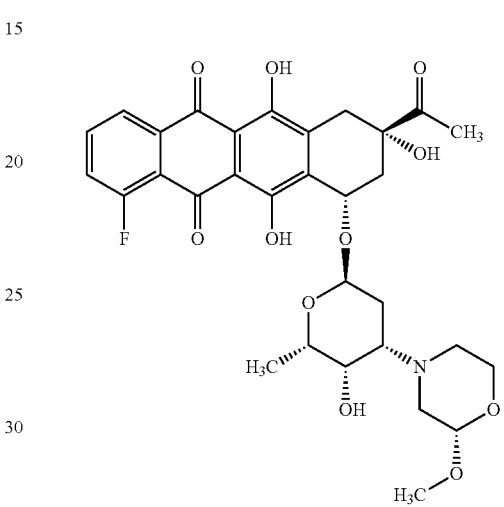

(1S,3S)-3-acetyl-10-fluoro-3,5,12-trihydroxy-6,11-dioxo-1,2,3,4,6,11-hexahydrotetracen-1-yl 3-amino-2,3,6-trideoxy-α-L-lyxo-hexopyranoside (70.0 mg, 0.136 mmol) [prepared as reported in WO90/09392] was dissolved in dry DMF (3 mL); a solution of diiso-propylethylamine (106 mg, 0.82 mmol) in dry DMF (2 mL) and a solution of (1S)-2-iodo-1-(2-iodoethoxy)-1-methoxyethane (IIa) (965 mg, 2.71 mmol) in dry DMF (10 ml) were added. The reaction mixture was stirred at room temperature in the dark for 48 hours, until no starting material was detectable (HPLC analysis). The reaction mixture was then diluted with DCM and washed with water. The organic phase was dried over anhydrous Na₂SO₄, the solvent was evaporated under vacuum and the residue was purified by flash chromatography (eluant: EtOH/DCM; 0.2/9.8) on silica gel (230-400 mesh) affording the desired product (35 mg, red wax).

ESI MS: m/z 616 (MH⁺)

¹H NMR (500 MHz, CHCl₃-d) δ ppm 1.39 (d, J=6.71 Hz, 3H) 1.78-1.85 (m, 2H) 2.09-2.14 (m, 1H) 2.46-2.56 (m, 3H) 2.61 (dd, J=11.41, 3.97 Hz, 1H) 3.03 (d, J=19.04 Hz, 1H) 3.27 (dd, J=19.10, 1.77 Hz, 1H) 3.40 (s, 3H) 3.57 (ddd, J=11.57, 5.34, 3.11 Hz, 1H) 3.70 (s, 1H) 3.92-3.99 (m, 1H) 4.04 (q, J=6.47 Hz, 1H) 4.48-4.52 (m, 1H) 4.67 (s, 1H) 5.28-5.30 (m, 1H) 5.56 (br. s., 1H) 7.54 (dd, J=10.44, 8.48 Hz, 1H) 7.83 (td, J=7.97, 4.58 Hz, 1H) 8.25 (d, J=7.69 Hz, 1H) 13.31 (s, 1H) 13.72 (s, 1H)

By analogous procedure the following compound is prepared:

(1S,3S)-10-fluoro-3,5,12-trihydroxy-3-(hydroxyacetyl)-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside [(III)]

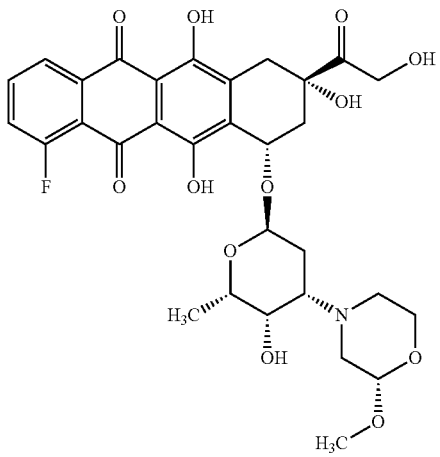 [SMILES: CO[C@@H]1CN([C@H]2C[C@H](O[C@H]3C[C@](O)(C(=O)CO)Cc4c(O)c5c(c(O)c43)C(=O)c3c(F)cccc3C5=O)O[C@@H](C)[C@H]2O)CCO1]

ESI MS: m/z 632 (MH+)

Step B3 (A6a)

(1S,3S)-3-acetyl-10-fluoro-3,5,12-trihydroxy-6,11-dioxo-1,2,3,4,6,11-hexahydrotetracen-1-yl (3ξ)-2,3,6-trideoxy-3-[(2S)-2-methoxy-4-oxidomorpholin-4-yl]-α-L-threo-hexopyranoside [(XX)]

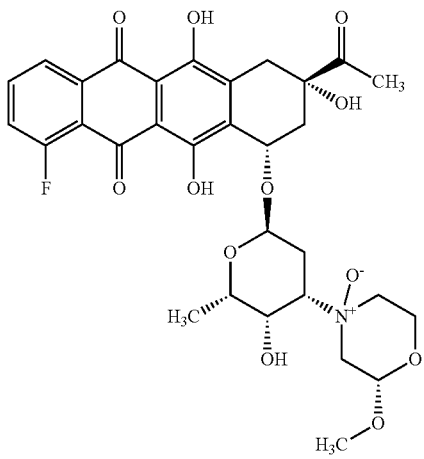 [SMILES: CO[C@@H]1C[N+]([O-])([C@H]2C[C@H](O[C@H]3C[C@](O)(C(C)=O)Cc4c(O)c5c(c(O)c43)C(=O)c3c(F)cccc3C5=O)O[C@@H](C)[C@H]2O)CCO1]

(1S,3S)-3-acetyl-10-fluoro-3,5,12-trihydroxy-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside (28 mg, 0.045 mmol) [prepared as reported in step A1] was dissolved in DCM (3.0 mL). The solution was treated with a 0.1 M solution of DMDO in acetone (0.8 mL) at room temperature for 30 minutes, until no starting material was detectable (HPLC analysis). The reaction mixture was then concentrated to dryness under vacuum, affording the desired intermediate (red wax, 24.1 mg).

ESI MS: m/z 632 (MH+)
$^1$H NMR (500 MHz, CH$_3$CN-d$_3$) δ ppm 1.23 (d, J=6.7 Hz, 3H) 1.96-2.00 (m, 1H) 2.10 (m, 1H) 2.35 (s, 3H) 2.33-2.38 (m, 1H) 2.56-2.64 (m, 2H) 2.94-3.00 (m, 1H) 3.07-3.12 (m, 1H) 3.13-3.16 (m, 1H) 3.23-3.29 (m, 1H) 3.37 (s, 3H) 3.38-3.46 (m, 2H) 3.86-3.95 (m, 1H) 3.99 (q, J=6.7 Hz, 1H) 4.14 (s, 1H) 4.22-4.29 (m, 1H) 4.32 (br. s., 1H) 4.91 (dd, J=8.1, 2.3 Hz, 1H) 5.20 (dd, J=4.6, 1.9 Hz, 1H) 5.60 (d, J=3.9 Hz, 1H) 7.62 (dd, J$_{HH}$=8.3, J$_{HF}$=10.8 Hz, 1H) 7.91 (m, 1H) 8.20 (d, J$_{HH}$=7.7 Hz, 1H) 13.26 (br. s., 1H) 13.69 (br. s., 1H)

By analogous procedure the following compound is prepared:

(1S,3S)-10-fluoro-3,5,12-trihydroxy-3-(hydroxyacetyl)-6,11-dioxo-1,2,3,4,6,11-hexahydrotetracen-1-yl (3ξ)-2,3,6-trideoxy-3-[(2S)-2-methoxy-4-oxidomorpholin-4-yl]-α-L-threo-hexopyranoside [(XX)]

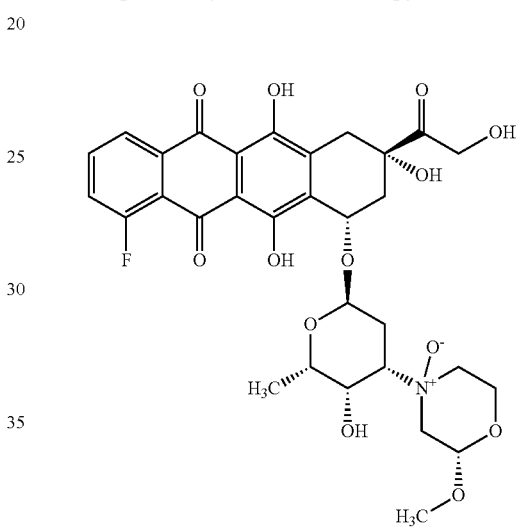

ESI MS: m/z 648 (MH+)

Step B3 (A6b)

The Title Compound (Compd. 1)

To a solution of compound (1S,3S)-3-acetyl-10-fluoro-3,5,12-trihydroxy-6,11-dioxo-1,2,3,4,6,11-hexahydrotetracen-1-yl (3ξ)-2,3,6-trideoxy-3-[(2S)-2-methoxy-4-oxidomorpholin-4-yl]-α-L-threo-hexopyranoside [(XX)] (20 mg, 0.032 mmol) in 5.0 ml of dry CH$_3$CN, K$_2$CO$_3$ (13.2 mg, 0.096 mmol) and cyanuric chloride (11.8 mg, 0.064 mmol) were added. The reaction mixture was vigorously stirred in the dark at room temperature for 20 minutes, until no starting material was detectable. A solution of 3-amino-1,2-propanediol (17.5 mg, 0.192 mmol) in water (0.84 ml) was then added to the reaction mixture and the aqueous phase was extracted with DCM (4×10 mL). The combined organic phases were dried over anhydrous Na$_2$SO$_4$, filtered and evaporated under vacuum. The crude was purified by flash column chromatography (AcOEt/toluene; 4/6) on silica gel (230-400 mesh), affording 7.0 mg of title compound as red solid.

ESI MS: m/z 614 (MH+)
$^1$H NMR (500 MHz, CH$_3$CN-d$_3$) δ ppm 1.29 (d, J=6.6 Hz, 3H) 1.68-1.73 (m, 1H) 1.86-1.91 (m, 1H) 2.05 (dd, J=14.8, 4.3 Hz, 1H) 2.34 (s, 3H) 2.42-2.47 (m, 1H) 2.67-2.81 (m, 2H) 2.93-2.98 (m, 1H) 3.05-3.11 (m, 1H) 3.37 (s, 3H)

3.42-3.47 (m, 1H) 3.52-3.58 (m, 1H) 3.71-3.76 (m, 1H) 4.03 (dd, J=7.1, 1.8 Hz, 1H) 4.06-4.12 (m, 1H) 4.26 (d, J=2.8 Hz, 1H) 4.53 (d, J=2.8 Hz, 1H) 4.54 (s, 1H) 5.20 (dd, J=4.3, 2.1 Hz, 1H) 5.35 (t, J=5.5 Hz, 1H) 7.60 (dd, $J_{HH}$=8.3, $J_{HF}$=11.6 Hz, 1H) 7.89 (m, 1H) 8.19 (dd, $J_{HH}$=7.7, $J_{HF}$=0.8 Hz, 1H) 13.25 (br. s., 1H) 13.61 (br. s., 1H)

Analogously, by using the suitable starting material, the following compounds are prepared:

(8S,10S)-1-fluoro-6,8,11-trihydroxy-8-(hydroxy-acetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 2)
[R1=F, R2=HOCH$_2$CO—, R3=CH$_3$O—]

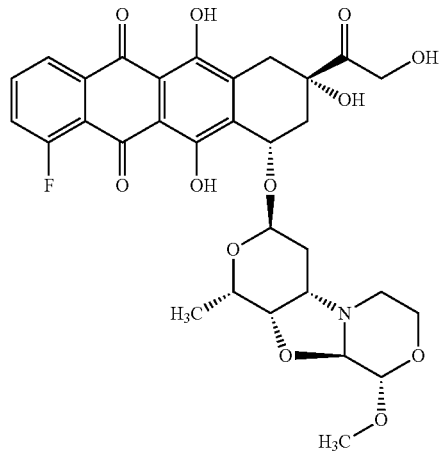 [SMILES: CO[C@H]1OCCN2[C@@H]1O[C@@H]1[C@H](C)O[C@@H](O[C@H]3C[C@](O)(C(=O)CO)Cc4c(O)c5c(c(O)c43)C(=O)c3c(F)cccc3C5=O)C[C@@H]12]

ESI MS: m/z 630 (MH$^+$)

(8S,10S)-8-acetyl-6,8,11-trihydroxy-1-[(2-hydroxy-ethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 5)
[R1=HO(CH$_2$)$_2$NH—, R2=CH$_3$CO—, R3=CH$_3$O—]

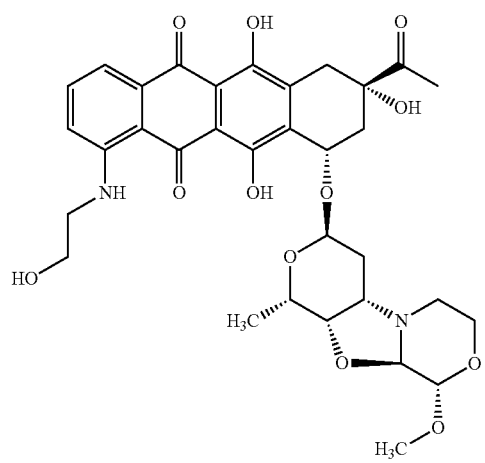 [SMILES: CO[C@H]1OCCN2[C@@H]1O[C@@H]1[C@H](C)O[C@@H](O[C@H]3C[C@](O)(C(C)=O)Cc4c(O)c5c(c(O)c43)C(=O)c3c(NCCO)cccc3C5=O)C[C@@H]12]

ESI MS: m/z 655 (MH$^+$)

(8S,10S)-6,8,11-trihydroxy-8-(hydroxyacetyl)-1-[(2-hydroxyethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 6)
[R1=HO(CH$_2$)$_2$NH—, R2=HOCH$_2$CO—, R3=CH$_3$O—]

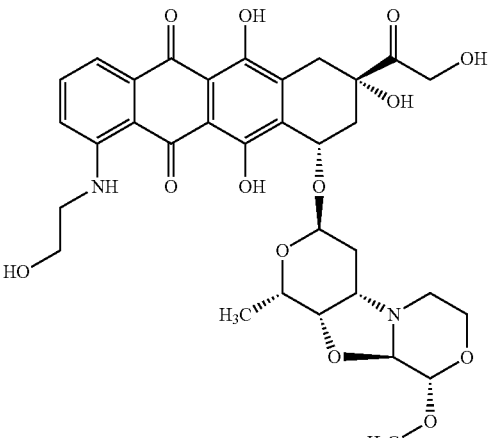

ESI MS: m/z 671 (MH$^+$)

(8S,10S)-8-acetyl-1-[(2-aminoethyl)amino]-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 7)
[R1=H$_2$N(CH$_2$)$_2$NH—, R2=CH$_3$CO—, R3=CH$_3$O—]

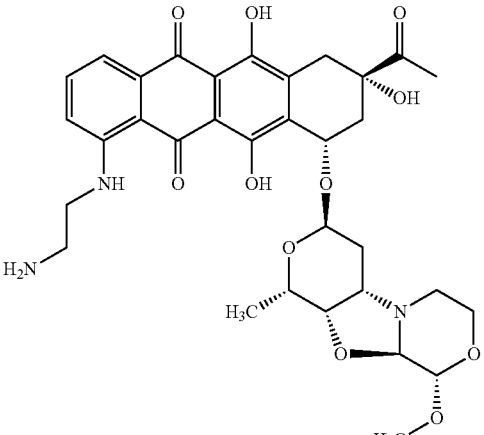

ESI MS: m/z 654 (MH$^+$)

39

(8S,10S)-1-[(2-aminoethyl)amino]-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 8)
[R1=H$_2$N(CH$_2$)$_2$NH—, R2=HOCH$_2$CO—, R3=CH$_3$O—]

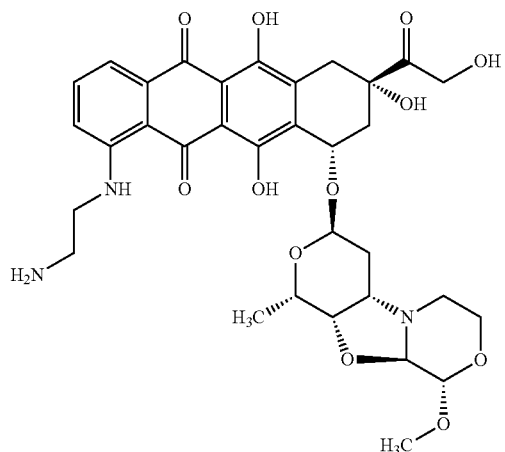

ESI MS: m/z 670 (MH$^+$)

Example 2

Step A1, Step B3 (According to A6a and A6b)

(8S,10S)-8-acetyl-1-amino-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [(I)] (compd. 4) [R1=NH$_2$—, R2=CH$_3$CO—, R3=CH$_3$O—]

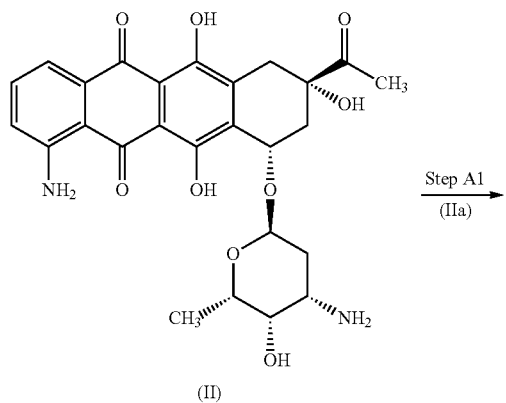

40

—continued

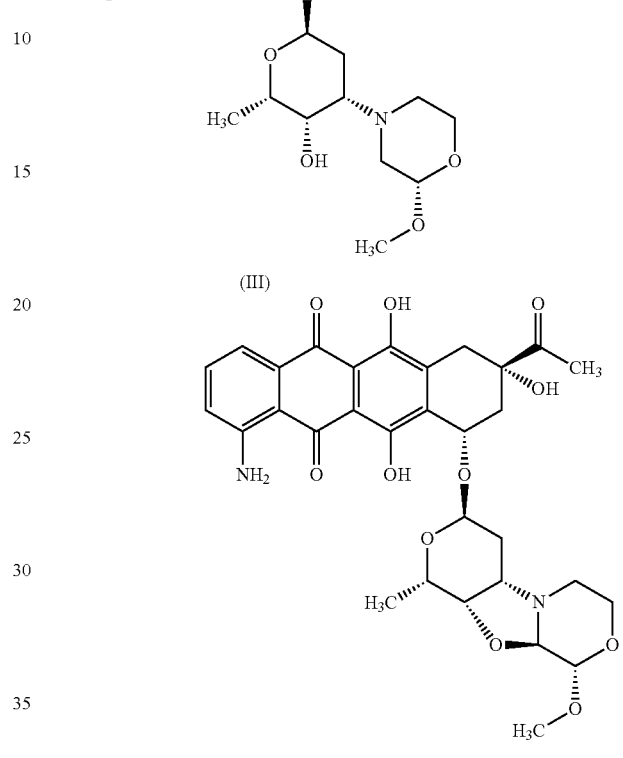

Step A1

(1S,3S)-3-acetyl-10-amino-3,5,12-trihydroxy-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside [(III)]

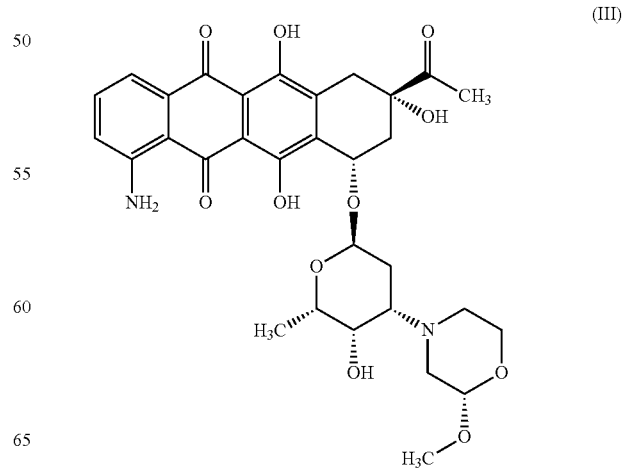

(1S,3S)-3-acetyl-10-amino-3,5,12-trihydroxy-6,11-dioxo-1,2,3,4,6,11-hexahydrotetracen-1-yl 3-amino-2,3,6-trideoxy-α-L-lyxo-hexopyranoside (165.0 mg, 0.322 mmol) [prepared as reported below in Example 3] was dissolved in dry DMF (3.0 mL); a solution of diiso-propylethylamine (221 mg, 1.71 mmol) in dry DMF (3 mL) and a solution of (1S)-2-iodo-1-(2-iodoethoxy)-1-methoxyethane (IIa) (2.0 g, 5.64 mmol) in dry DMF (10 mL) were added. The reaction mixture was stirred at room temperature in the dark for 48 hours, until no starting material was detectable (HPLC analysis). The reaction mixture was then diluted with DCM and washed with water. The organic phase was dried over anhydrous $Na_2SO_4$, the solvent was evaporated under vacuum and the residue was purified by flash chromatography (eluant: EtOH/DCM; 0.2/9.8) on silica gel (230-400 mesh) affording the desired product (105.0 mg, red solid).

ESI MS: m/z 613 (MH$^+$)

$^1$H NMR (500 MHz, $CH_3CN$-d$_3$) δ ppm 1.22-1.28 (m, 3H) 1.65-1.83 (m, 2H) 2.30-2.36 (m, 4H) 2.40 (dd, J=11.22, 4.94 Hz, 3H) 2.46-2.54 (m, 2H) 2.87-2.96 (m, 1H) 3.04-3.11 (m, 1H) 3.32 (s, 3H) 3.50 (ddd, J=11.34, 6.51, 2.83 Hz, 1H) 3.65 (br. s., 1H) 3.77-3.89 (m, 1H) 4.04 (d, J=6.51 Hz, 1H) 4.44 (dd, J=4.63, 2.41 Hz, 1H) 5.16 (d, J=1.99 Hz, 1H) 5.43-5.47 (m, 1H) 7.12-7.16 (m, 1H) 7.24 (br. s., 1H) 7.50-7.55 (m, 1H) 7.58-7.61 (m, 1H)

By analogous procedure the following compounds are prepared:

(1S,3S)-10-amino-3,5,12-trihydroxy-3-(hydroxyacetyl)-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside

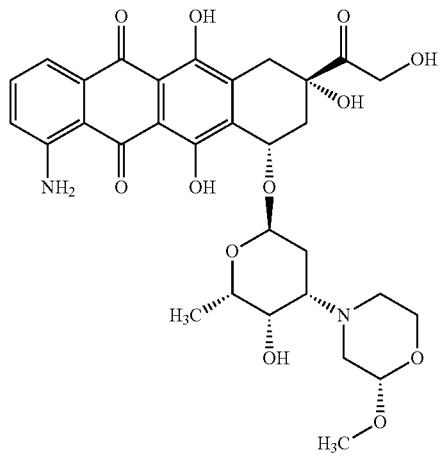

(III)

ESI MS: m/z 629 (MH$^+$)

Analogously, by using the suitable starting material, the following compounds are prepared:

(1S,3S)-3-acetyl-3,5,12-trihydroxy-10-[(2-hydroxyethyl)amino]-6,11-dioxo-1,2,3,4,6,11-hexahydrotetracen-1-yl 3-amino-2,3,6-trideoxy-L-lyxo-hexopyranoside

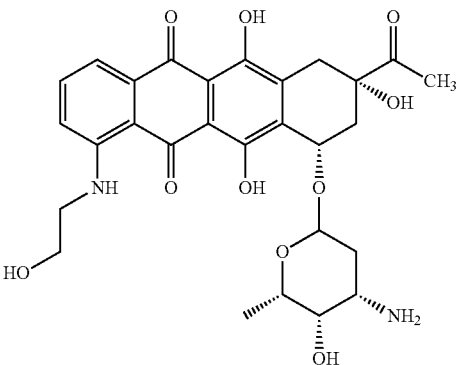 [SMILES: CC(=O)[C@]1(O)Cc2c(O)c3c(c(O)c2[C@@H](OC2C[C@H](N)[C@H](O)[C@H](C)O2)C1)C(=O)c1c(NCCO)cccc1C3=O]

ESI MS: m/z 557 (MH$^+$)

(1S,3S)-3-acetyl-10-[(2-aminoethyl)amino]-3,5,12-trihydroxy-6,11-dioxo-1,2,3,4,6,11-hexahydrotetracen-1-yl 3-amino-2,3,6-trideoxy-L-lyxo-hexopyranoside

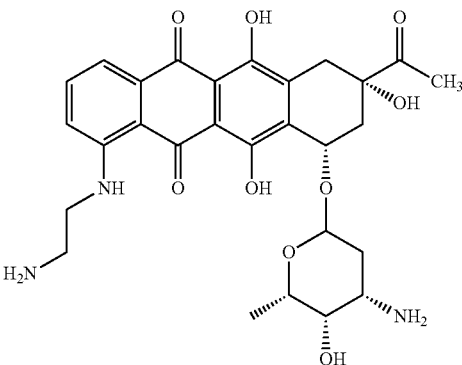 [SMILES: CC(=O)[C@]1(O)Cc2c(O)c3c(c(O)c2[C@@H](OC2C[C@H](N)[C@H](O)[C@H](C)O2)C1)C(=O)c1c(NCCN)cccc1C3=O]

ESI MS: m/z 556 (MH$^+$)

Protection

N-[(8S,10S)-8-acetyl-6,8,11-trihydroxy-5,12-dioxo-10-({2,3,6-trideoxy-3-[(2S)-2-methoxymorpholin-4-yl]- -L-lyxo-hexopyranosyl}oxy)-5,7,8,9,10,12-hexahydrotetracen-1-yl]-2,2,2-trifluoroacetamide Step B3 (A6a)

N-[(8S,10S)-8-acetyl-6,8,11-trihydroxy-5,12-dioxo-10-({(3ξ)-2,3,6-trideoxy-3-[(2S)-2-methoxy-4-oxidomorpholin-4-yl]-α-L-threo-hexopyranosyl}oxy)-5,7,8,9,10,12-hexahydrotetracen-1-yl]-2,2,2-trifluoroacetamide [(XX)]

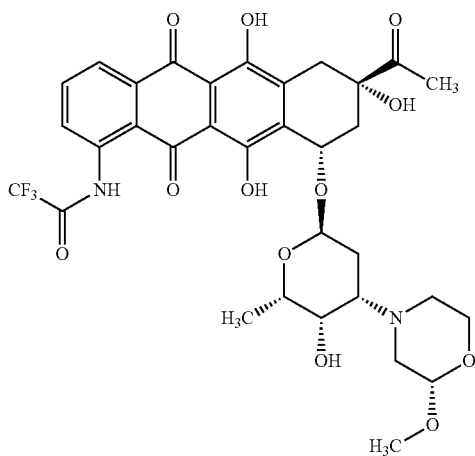 [SMILES: CO[C@@H]1CN([C@H]2C[C@H](O[C@H]3C[C@](O)(C(C)=O)Cc4c(O)c5c(c(O)c43)C(=O)c3c(NC(=O)C(F)(F)F)cccc3C5=O)O[C@@H](C)[C@H]2O)CCO1]

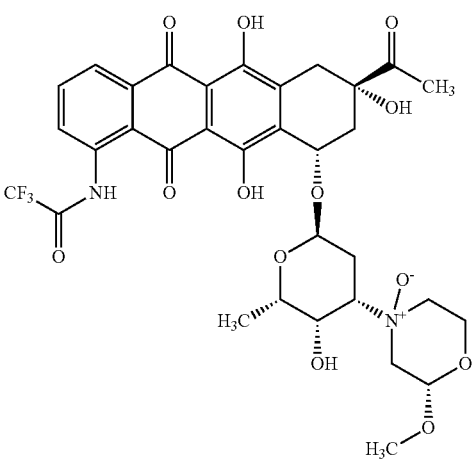 [SMILES: CO[C@@H]1C[N+]([O-])([C@H]2C[C@H](O[C@H]3C[C@](O)(C(C)=O)Cc4c(O)c5c(c(O)c43)C(=O)c3c(NC(=O)C(F)(F)F)cccc3C5=O)O[C@@H](C)[C@H]2O)CCO1]

(1S,3S)-3-acetyl-10-amino-3,5,12-trihydroxy-6,11-dioxo-1,2,3,4,6,11-hexahydrotetracen-1-yl 2,3,6-trideoxy-3-[(2S)-2-methoxymorpholin-4-yl]-α-L-lyxo-hexopyranoside [(III)] (80.0 mg, 0.130 mmol) was dissolved in dry DCM (11 mL) and trifluoroacetic anhydride (273.0 mg, 1.3 mmol) was added. The reaction mixture was stirred at room temperature in the dark for 30 minutes, until no starting material was detectable (HPLC analysis). The reaction mixture was then diluted with DCM and washed with saturated NaHCO₃ aqueous solution (3×10 mL), and then with water (1×10 mL). The organic phase was dried over anhydrous Na₂SO₄, the solvent was evaporated under vacuum and the residue thus obtained was treated with MeOH (10 mL) at room temperature for 15 minutes, and then evaporated under vacuum affording the desired product (77.0 mg, red wax).

ESI MS: m/z 709 (MH⁺)

$^1$H NMR (500 MHz, CH₃CN-d₃) δ ppm 1.25 (d, J=6.59 Hz, 3H) 1.76 (dd, J=8.68, 2.61 Hz, 2H) 2.27-2.45 (m, 8H) 2.52 (t, J=10.99 Hz, 2H) 2.96-3.03 (m, 1H) 3.08-3.15 (m, 1H) 3.30-3.33 (m, 3H) 3.50 (ddd, J=11.27, 6.57, 2.61 Hz, 1H) 3.66 (br. s., 1H) 3.79-3.87 (m, 1H) 4.05 (q, J=6.62 Hz, 1H) 4.44 (dd, J=4.70, 2.35 Hz, 1H) 5.17 (d, J=2.27 Hz, 1H) 5.45 (s, 1H) 7.97 (t, J=8.15 Hz, 1H) 8.24 (d, J=7.50 Hz, 1H) 8.99 (d, J=8.18 Hz, 1H)

N-[(8S,10S)-8-acetyl-6,8,11-trihydroxy-5,12-dioxo-10-({2,3,6-trideoxy-3-[(2S)-2-methoxymorpholin-4-yl]-α-L-lyxo-hexopyranosyl}oxy)-5,7,8,9,10,12-hexahydrotetracen-1-yl]-2,2,2-trifluoroacetamide (72.0 mg, 0.102 mmol) was dissolved in DCM (6.4 mL). The solution was treated with a 0.1 M solution of DMDO in acetone (1.7 mL) at room temperature for 30 minutes, until no starting material was detectable (HPLC analysis). The reaction mixture was then concentrated to dryness under vacuum, affording the desired intermediate (red wax, 73.0 mg).

ESI MS: m/z 725 (MH⁺)

$^1$H NMR (500 MHz, CH₃CN-d₃) δ ppm 1.23 (d, J=6.51 Hz, 3H) 2.32-2.39 (m, 4H) 2.57 (d, J=4.54 Hz, 1H) 2.74 (d, J=11.65 Hz, 1H) 2.96-3.02 (m, 1H) 3.08-3.15 (m, 1H) 3.25-3.45 (m, 7H) 3.57 (br. s., 1H) 3.92 (d, J=12.79 Hz, 1H) 4.04 (d, J=6.88 Hz, 1H) 4.18 (s, 1H) 4.21-4.28 (m, 1H) 4.92 (dd, J=8.21, 2.08 Hz, 1H) 5.19 (d, J=2.19 Hz, 1H) 5.61 (d, J=3.71 Hz, 1H) 7.97 (t, J=8.10 Hz, 1H) 8.23 (d, J=7.64 Hz, 1H) 8.98 (d, J=8.32 Hz, 1H)

By analogous procedure the following compound can be prepared:

(1S,3S)-10-amino-3,5,12-trihydroxy-3-(hydroxyacetyl)-6,11-dioxo-1,2,3,4,6,11-hexahydrotetracen-1-yl (3ξ)-2,3,6-trideoxy-3-[(2S)-2-methoxy-4-oxidomorpholin-4-yl]-α-L-threo-hexopyranoside [(XX)]

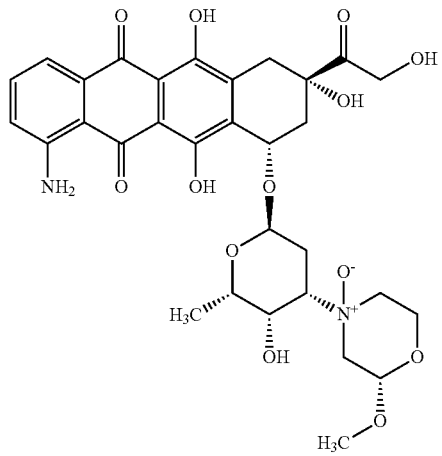 [SMILES: CO[C@@H]1C[N+]([O-])([C@H]2C[C@H](O[C@H]3C[C@](O)(C(=O)CO)Cc4c(O)c5c(c(O)c43)C(=O)c3c(N)cccc3C5=O)O[C@@H](C)[C@H]2O)CCO1]

ESI MS: m/z 645 (MH⁺)

Step B3 (A6b)

N-[(8S,10S)-8-acetyl-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-5,12-dioxo-5,7,8,9,10,12-hexahydrotetracen-1-yl]-2,2,2-trifluoroacetamide [(I)]

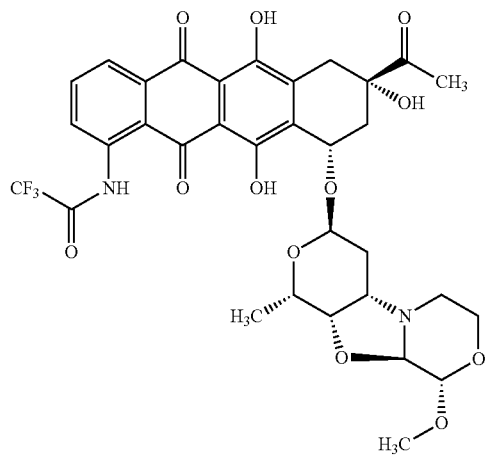 [SMILES: CO[C@H]1OCCN2[C@@H]1O[C@@H]1[C@H](C)O[C@@H](O[C@H]3C[C@](O)(C(C)=O)Cc4c(O)c5c(c(O)c43)C(=O)c3c(NC(=O)C(F)(F)F)cccc3C5=O)C[C@@H]12]

To a solution of compound N-[(8S,10S)-8-acetyl-6,8,11-trihydroxy-5,12-dioxo-10-({(3ξ)-2,3,6-trideoxy-3-[(2S)-2-methoxy-4-oxidomorpholin-4-yl]-α-L-threo-hexopyranosyl}oxy)-5,7,8,9,10,12-hexahydrotetracen-1-yl]-2,2,2-trifluoroacetamide [(XX)] (60.0 mg, 0.083 mmol) in 13 mL of dry CH₃CN, K₂CO₃ (34.4 mg, 0.249 mmol) and cyanuric chloride (30.6 mg, 0.166 mmol) were added. The reaction mixture was vigorously stirred in the dark at room temperature for 15 minutes, until no starting material was detectable. A solution of 3-amino-1,2-propanediol (45.3 mg, 0.5 mmol) in water (0.22 mL) was then added to the reaction mixture and the aqueous phase was extracted with DCM (4×10 mL). The combined organic phases were dried over anhydrous Na₂SO₄, filtered and evaporated under vacuum. The crude was purified by flash column chromatography (AcOEt/toluene; 4/6) on silica gel (230-400 mesh), affording 12.0 mg of title compound as red solid.

ESI MS: m/z 707 (MH⁺)

¹H NMR (500 MHz, CH₃CN-d₃) δ ppm 1.29 (d, J=6.58 Hz, 4H) 1.70 (d, J=15.21 Hz, 1H) 1.90 (d, J=15.59 Hz, 2H) 2.04-2.08 (m, 2H) 2.45 (d, J=14.98 Hz, 1H) 2.69-2.76 (m, 1H) 2.77-2.83 (m, 1H) 2.97 (s, 1H) 3.08-3.14 (m, 2H) 3.38 (s, 4H) 3.45 (d, J=6.88 Hz, 2H) 3.56 (d, J=5.22 Hz, 2H) 3.74 (s, 1H) 4.04 (d, J=1.89 Hz, 2H) 4.09 (d, J=6.88 Hz, 1H) 4.26 (d, J=2.72 Hz, 1H) 4.52-4.54 (m, 2H) 5.22 (br. s., 1H) 5.36 (t, J=5.60 Hz, 1H) 7.98 (t, J=8.06 Hz, 1H) 8.26 (d, J=7.87 Hz, 1H) 9.00 (d, J=8.10 Hz, 1H)

Deprotection

The Title Compound (Compd.4)

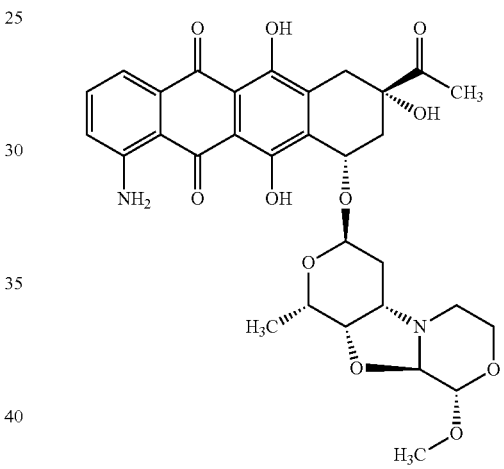

The N-[(8S,10S)-8-acetyl-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-5,12-dioxo-5,7,8,9,10,12-hexahydrotetracen-1-yl]-2,2,2-trifluoroacetamide intermediate (4.8 mg, 0.00679 mmol) was cooled at 0° C. and 0.1 N NaOH aqueous solution (0.5 mL) was added. The reaction mixture was stirred in the dark 0° C. for 15 minutes, until no starting material was detectable. The reaction mixture was then diluted with H₂O and extracted with DCM (4×5 mL). The combined organic phases were washed with saturated aqueous NaCl solution (1×10 mL), dried over anhydrous Na₂SO₄, filtered and evaporated under vacuum, affording 4.0 mg of title compound as red solid.

ESI MS: m/z 611 (MH⁺)

¹H NMR (500 MHz, CH₃CN-d₃) δ ppm 1.70 (dt, J=15.06, 5.82 Hz, 2H) 1.87 (dt, J=15.17, 5.54 Hz, 1H) 2.34 (s, 3H) 2.43 (d, J=14.41 Hz, 1H) 2.68-2.81 (m, 2H) 2.91-2.96 (m, 1H) 3.07 (d, J=18.66 Hz, 1H) 3.37 (s, 3H) 3.44 (q, J=5.87 Hz, 1H) 3.51-3.61 (m, 2H) 3.74 (ddd, J=11.63, 8.25, 2.96 Hz, 1H) 4.01-4.04 (m, 1H) 4.06-4.13 (m, 1H) 4.26 (d, J=2.66 Hz, 1H) 4.54 (d, J=2.58 Hz, 1H) 5.21 (br. s., 1H) 5.37 (t, J=5.61 Hz, 1H) 7.16 (d, J=8.57 Hz, 1H) 7.54 (t, J=7.89 Hz, 1H) 7.62 (d, J=7.06 Hz, 1H)

Analogously, by using the suitable starting material, the following compound is prepared:

(8S,10S)-1-amino-6,8,11-trihydroxy-8-(hydroxy-acetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione (compd. 3)
[R1=NH₂—, R2=HOCH₂CO—, R3=CH₃O— ]

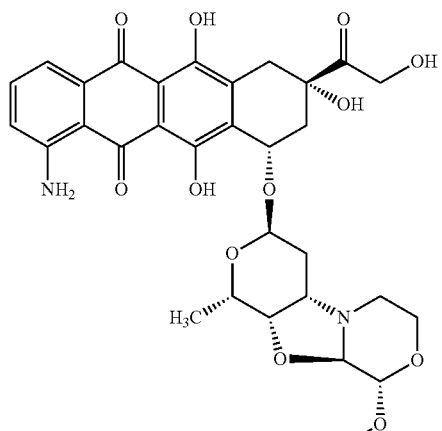

(III)

ESI MS: m/z 627 (MH⁺)

Example 3

Preparation of the Intermediates of Formula (II)

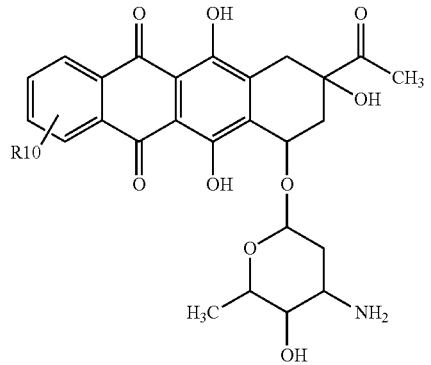

(II)

Step G2, Deprotection, Protection, Step G3, Deprotection

Synthesis of (1S,3S)-3-acetyl-10-amino-3,5,12-trihydroxy-6,11-dioxo-1,2,3,4,6,11-hexahydrotetracen-1-yl 3-amino-2,3,6-trideoxy-L-lyxo-hexopyranoside

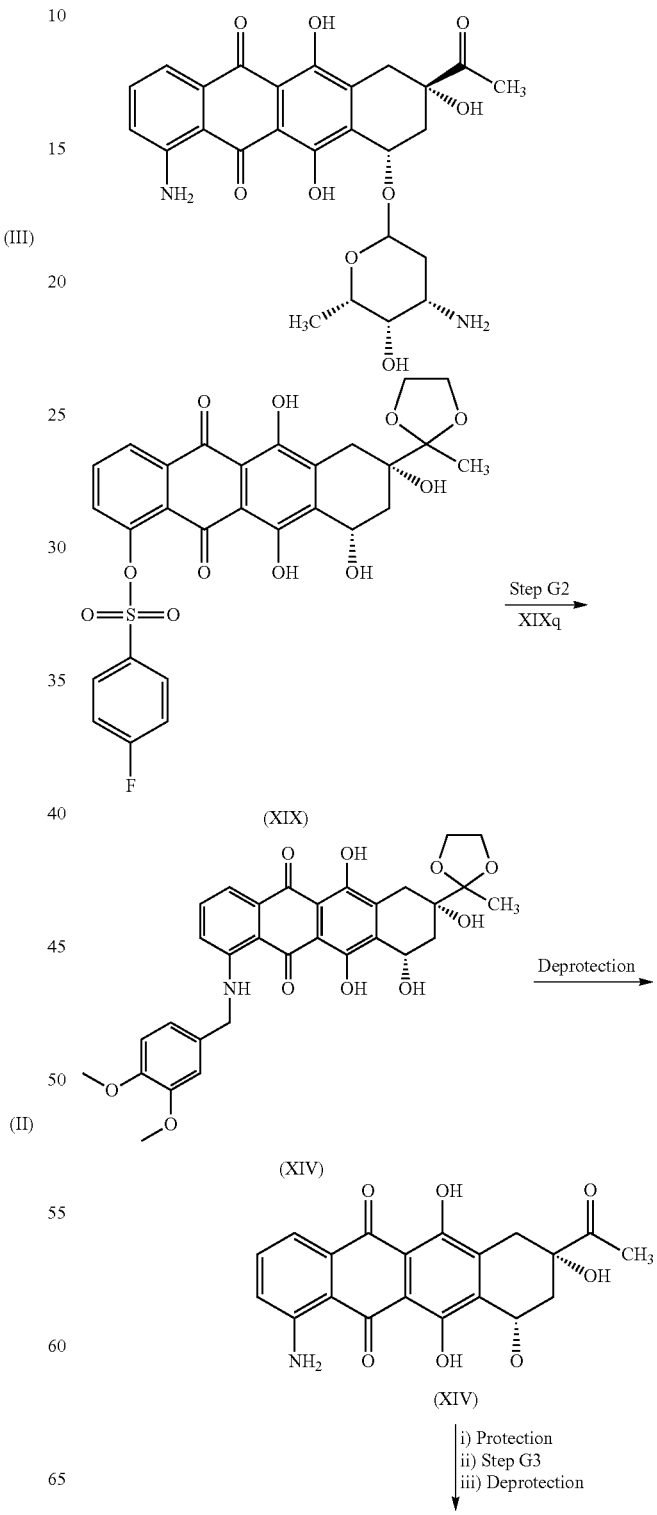

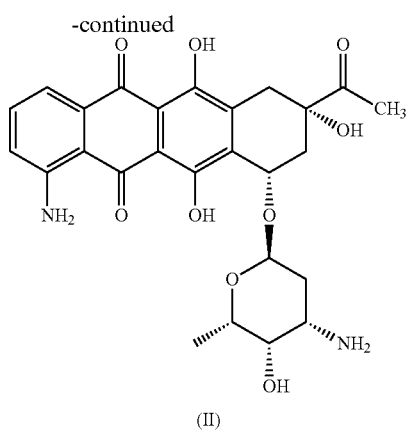

(II)

Step G2

Synthesis of the intermediate (8S,10S)-1-[(3,4-dimethoxybenzyl)amino]-6,8,10,11-tetrahydroxy-8-(2-methyl-1,3-dioxolan-2-yl)-7,8,9,10-tetrahydrotetracene-5,12-dione (XIV)

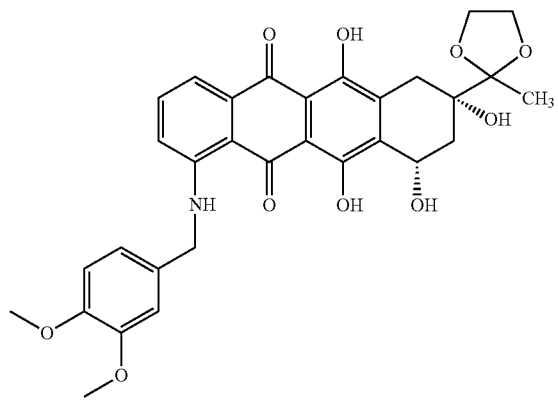

To a solution of (8S,10S)-6,8,10,11-tetrahydroxy-8-(2-methyl-1,3-dioxolan-2-yl)-5,12-dioxo-5,7,8,9,10,12-hexahydrotetracen-1-yl 4-fluorobenzenesulfonate (400 mg, 0.682 mmol) [prepared as reported in GB2215332] in THF (10 mL), 3-4 dimethoxybenzylamine (0.532 mg, 3.1 mmol) was added. The solution was heated at 60° C. and stirred for 24 hours in the dark. Then, the solvent was partially removed under vacuum, the dark violet precipitate collected by filtration, washed with THF (3 mL) and then with Et$_2$O (10 mL). The solid was finally dried in the oven under vacuum at 30° C. to yield the title intermediate (188 mg, y=48%).

Analogously, by using the suitable amines, the following compounds are prepared:

(8S,10S)-6,8,10,11-tetrahydroxy-1-[(2-hydroxyethyl)amino]-8-(2-methyl-1,3-dioxolan-2-yl)-7,8,9,10-tetrahydrotetracene-5,12-dione

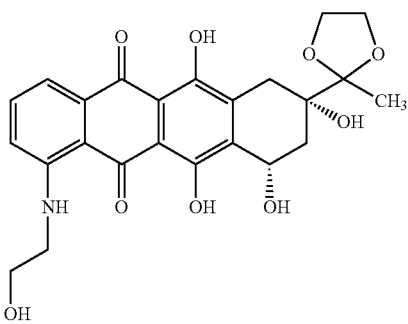 [SMILES: CC1([C@]2(O)Cc3c(O)c4c(c(O)c3[C@@H](O)C2)C(=O)c2c(NCCO)cccc2C4=O)OCCO1]

ESI MS: m/z 472 (MH$^+$)

$^1$H NMR (499.75 MHz, DMSO-d$_6$) δ ppm 1.33 (s, 3H), 1.82 (dd, J=14.3, 4.3 Hz, 1H), 2.20 (d, J=14.3 Hz, 1H), 2.67 (d, J=18.7 Hz, 1H), 3.10 (d, J=18.7 Hz, 1H), 3.45-3.49 (m, 2H), 3.68-3.72 (m, 2H), 3.92-4.01 (m, 4H), 5.00 (t, J=5.1 Hz, 1H), 5.05-5.11 (m, 1H), 5.35 (d, J=7.6 Hz, 1H), 5.44 (s, 1H), 7.35 (d, J=8.7 Hz, 1H), 7.56 (d, J=6.8 Hz, 1H), 7.70 (dd, J=8.7, 6.8 Hz, 1H), 9.61 (t, J=5.1 Hz, 1H), 13.52 (br. s., 1H), 13.74 (br. s., 1H)

(8S,10S)-1-[(2-aminoethyl)amino]-6,8,10,11-tetrahydroxy-8-(2-methyl-1,3-dioxolan-2-yl)-7,8,9,10-tetrahydrotetracene-5,12-dione

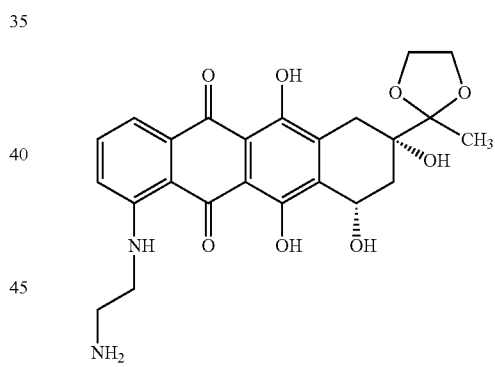

ESI MS: m/z 471 (MH$^+$)

Deprotection

Synthesis of the intermediate (8S,10S)-8-acetyl-1-amino-6,8,10,11-tetrahydroxy-7,8,9,10-tetrahydrotetracene-5,12-dione (XIV)

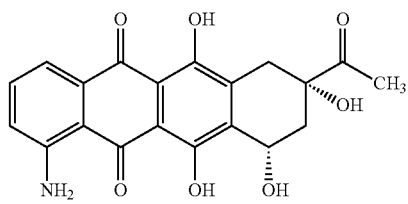 [SMILES: CC(=O)[C@]1(O)Cc2c(O)c3c(c(O)c2[C@@H](O)C1)C(=O)c1c(N)cccc1C3=O]

To cold trifluoroacetic acid (2 mL), (8S,10S)-1-[(3,4-dimethoxybenzyl)amino]-6,8,10,11-tetrahydroxy-8-(2-methyl-1,3-dioxolan-2-yl)-7,8,9,10-tetrahydrotetracene-5,12-dione (133 mg, 0.230 mmol) and 2 drops of anisole were added. The solution was stirred at 5° C. for 20 min and then at room temperature for 2 hours until no starting material was detectable. The reaction was diluted with water (5 mL), neutralized with NaHCO$_3$ solution then, the aqueous phase extracted with DCM (3×50 mL). The combined organic phases were dried over anhydrous Na$_2$SO$_4$, filtered, the solvent evaporated under vacuum and the crude treated with Et$_2$O (10 mL). The dark violet precipitate was collected by filtration and dried in the oven under vacuum at 30° C. to yield the desired intermediate (82 mg, y=93%).

ESI MS: m/z 384 (MH$^+$)

$^1$H NMR (400.5 MHz, DMSO-d$_6$) δ ppm 1.99 (dd, J=14.4, 4.6 Hz, 1H), 2.13-2.19 (m, 1H), 2.30 (s, 3H), 2.88-2.95 (m, 1H), 2.98-3.05 (m, 1H), 5.07 (m, 1H), 5.29 (br. s., 1H), 6.07 (s, 1H), 7.24 (dd, J=8.3, 1.1 Hz, 1H), 7.51 (dd, J=7.3, 1.1 Hz, 1H), 7.55-7.60 (m, 1H), 8.05 (br. s., 2H), 13.49 (br. s., 1H), 13.85 (br. s., 1H)

Analogously, by using the suitable starting material, the following compounds can be prepared:

(8S,10S)-8-acetyl-6,8,10,11-tetrahydroxy-1-[(2-hydroxyethyl)amino]-7,8,9,10-tetrahydrotetracene-5,12-dione

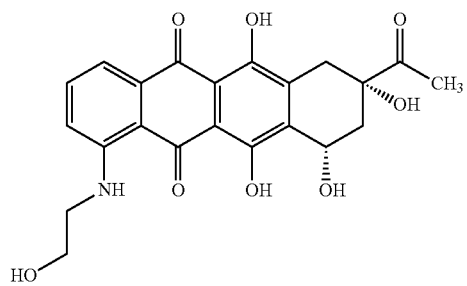 [SMILES: CC(=O)[C@]1(O)Cc2c(O)c3c(c(O)c2[C@@H](O)C1)C(=O)c1c(NCCO)cccc1C3=O]

ESI MS: m/z 428 (MH$^+$)

$^1$H NMR (500 MHz, DMSO-d$_6$) δ ppm 1.98 (dd, J=14.2, 4.6 Hz, 1H), 2.16 (d, J=14.2 Hz, 1H), 2.31 (s, 3H), 2.88-2.94 (m, 1H), 2.98-3.04 (m, 1H), 3.46-3.49 (m, 2H), 3.68-3.72 (m, 2H), 5.01 (t, J=5.1 Hz, 1H), 5.05-5.10 (m, 1H), 5.30 (d, J=6.7 Hz, 1H), 6.10 (s, 1H), 7.35 (d, J=8.7 Hz, 1H), 7.56 (d, J=7.1 Hz, 1H), 7.70 (dd, J=8.7, 7.1 Hz, 1H), 9.62 (t, J=5.1 Hz, 1H), 13.47 (br. s., 1H), 13.76 (br. s., 1H)

(8S,10S)-8-acetyl-1-[(2-aminoethyl)amino]-6,8,10,11-tetrahydroxy-7,8,9,10-tetrahydrotetracene-5,12-dione

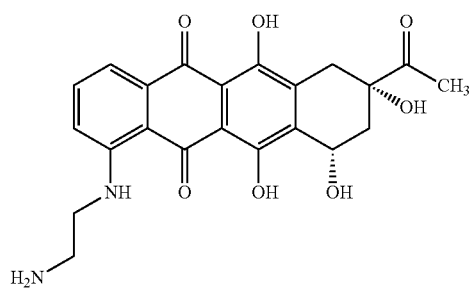 [SMILES: CC(=O)[C@]1(O)Cc2c(O)c3c(c(O)c2[C@@H](O)C1)C(=O)c1c(NCCN)cccc1C3=O]

ESI MS: m/z 427 (MH$^+$)

$^1$H NMR (500 MHz, DMSO-d$_6$) δ ppm 1.97 (dd, J=14.2, 4.6 Hz, 1H), 2.14 (d, J=14.2 Hz, 1H), 2.31 (s, 3H), 2.88-2.94 (m, 1H), 2.98-3.04 (m, 1H), 3.05-3.22 (m, 4H), 5.05-5.10 (m, 1H), 5.30 (d, J=6.7 Hz, 1H), 6.10 (s, 1H), 7.35 (d, J=8.7 Hz, 1H), 7.54 (d, J=7.1 Hz, 1H), 7.70 (dd, J=8.7, 7.1 Hz, 1H), 9.60 (t, J=5.1 Hz, 1H), 13.46 (br. s., 1H), 13.76 (br. s., 1H)

Protection

Synthesis of the intermediate N-[(8S,10S)-8-acetyl-6,8,10,11-tetrahydroxy-5,12-dioxo-5,7,8,9,10,12-hexahydrotetracen-1-yl]-2,2,2-trifluoroacetamide

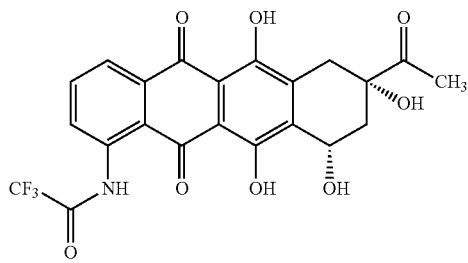 [SMILES: CC(=O)[C@]1(O)Cc2c(O)c3c(c(O)c2[C@@H](O)C1)C(=O)c1c(NC(=O)C(F)(F)F)cccc1C3=O]

The intermediate (8S,10S)-8-acetyl-1-amino-6,8,10,11-tetrahydroxy-7,8,9,10-tetrahydrotetracene-5,12-dione (600.0 mg, 1.56 mmol) was dissolved in dry DCM (120 mL) and trifluoroacetic anhydride (1.2 mL) was added. The reaction mixture was stirred at room temperature in the dark for 5 minutes, until no starting material was detectable (HPLC analysis). The reaction mixture was then diluted with DCM (100 mL) and washed with saturated NaHCO$_3$ aqueous solution (3×100 mL), and then with water (1×100 mL). The organic phase was dried over anhydrous Na$_2$SO$_4$, and the solvent was removed under vacuum. The residue thus obtained was purified by flash chromatography (eluant: CH$_3$COCH$_3$/DCM; 0.3/9.7) on silica gel (230-400 mesh) affording the desired product (494.1 mg, red solid).

ESI MS: m/z 480 (MH$^+$)

$^1$H NMR (500 MHz, CHCl$_3$-d) δ ppm 2.22 (dd, J=14.5, 4.9 Hz, 1H), 2.36-2.41 (m, 1H), 2.45 (s, 3H), 3.01 (d, J=18.7 Hz, 1H), 3.23 (dd, J=18.7, 2.2 Hz, 1H), 3.81 (d, J=5.2 Hz, 1H), 4.54 (s, 1H), 5.35 (m, 1H), 7.93 (dd, J=8.4, 7.7 Hz, 1H), 8.29 (dd, J=7.7, 1.1 Hz, 1H), 9.12 (dd, J=8.4, 1.1 Hz, 1H), 13.29 (br.s., 1H), 13.29 (s, 1H), 13.46 (s, 1H).

Analogously, by using the suitable starting material, the following compound is prepared:

N-(2-{[(8S,10S)-8-acetyl-6,8,10,11-tetrahydroxy-5,12-dioxo-5,7,8,9,10,12-hexahydrotetracen-1-yl]amino}ethyl)-2,2,2-trifluoroacetamide

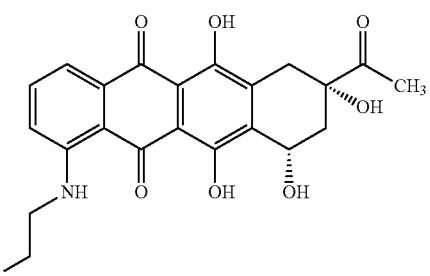

ESI MS: m/z 523 (MH$^+$)

Step G3

Synthesis of N-[(8S,10S)-8-acetyl-6,8,11-trihydroxy-5,12-dioxo-10-({2,3,6-trideoxy-3-[(trifluoroacetyl)amino]-L-lyxo-hexopyranosyl}oxy)-5,7,8,9,10,12-hexahydrotetracen-1-yl]-2,2,2-trifluoroacetamide

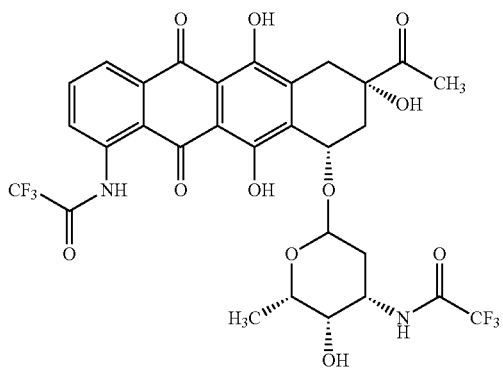 [SMILES: CC(=O)[C@]1(O)Cc2c(O)c3c(c(O)c2[C@@H](OC2C[C@H](NC(=O)C(F)(F)F)[C@H](O)[C@H](C)O2)C1)C(=O)c1c(NC(=O)C(F)(F)F)cccc1C3=O]

In a dry three-necked round-bottomed flask under argon atmosphere, the intermediate N-[(8S,10S)-8-acetyl-6,8,10,11-tetrahydroxy-5,12-dioxo-5,7,8,9,10,12-hexahydrotetracen-1-yl]-2,2,2-trifluoroacetamide (480.0 mg, 1.0 mmol) was dissolved in dry DCM (110 mL), and powdered molecular sieves (4 Å, 20.0 mg) were added. The reaction mixture was cooled at 10° C.; the solution of silver trifluoromethanesulfonate (334.0 mg, 1.3 mmol) in dry Et$_2$O (15 mL) and the solution of 2,3,6-trideoxy-4-O-(trifluoroacetyl)-3-[(trifluoroacetyl)amino]-δ-L-lyxo-hexopyranosyl chloride (511.4 mg, 1.43 mmol) in dry DCM (15 mL) were simultaneously added. The reaction mixture was stirred at 10° C. in the dark for 45 minutes, until no starting material was detectable (HPLC analysis). Saturated NaHCO$_3$ aqueous solution (50 mL) was added and the reaction mixture was stirred at room temperature for 30 minutes, and then filtered through a celite pad. The organic phase was separated, washed with water and dried over anhydrous Na$_2$SO$_4$. The solvent was removed under vacuum, and the residue thus obtained was cooled at 0° C. and treated with MeOH (20 mL) and solid NaHCO$_3$ for 15 minutes. The solvent was evaporated under vacuum and the residue was purified by flash chromatography (eluant: CH$_3$COCH$_3$/DCM; 0.5/9.5) on silica gel (230-400 mesh) affording the desired product (320.0 mg, red solid).

ESI MS: m/z 705 (MH$^+$)

$^1$H NMR (500 MHz, CH$_3$CN-d$_3$) δ ppm 1.22 (d, J=6.47 Hz, 3H) 1.77 (dd, J=13.18, 4.64 Hz, 1H) 2.00 (td, J=13.15, 3.97 Hz, 1H) 2.10 (d, J=10.13 Hz, 1H) 2.33-2.35 (m, 1H) 2.87-3.00 (m, 1H) 3.01-3.13 (m, 1H) 3.22 (br. s., 1H) 3.61 (br. s., 1H) 4.09-4.16 (m, 1H) 4.22 (q, J=6.47 Hz, 1H) 4.29 (s, 1H) 5.10 (br. s., 1H) 5.40 (d, J=3.54 Hz, 1H) 7.32 (d, J=7.81 Hz, 1H) 7.89 (t, J=7.63 Hz, 1H) 8.11 (d, J=7.08 Hz, 1H) 8.89 (d, J=8.30 Hz, 1H) 13.08 (br. s., 2H)

Analogously, by using the suitable starting material, the following compounds are prepared:

N-(2-{[(8S,10S)-8-acetyl-6,8,11-trihydroxy-5,12-dioxo-10-({2,3,6-trideoxy-3-[(trifluoroacetyl)amino]-L-lyxo-hexopyranosyl}oxy)-5,7,8,9,10,12-hexahydrotetracen-1-yl]amino}ethyl)-2,2,2-trifluoroacetamide

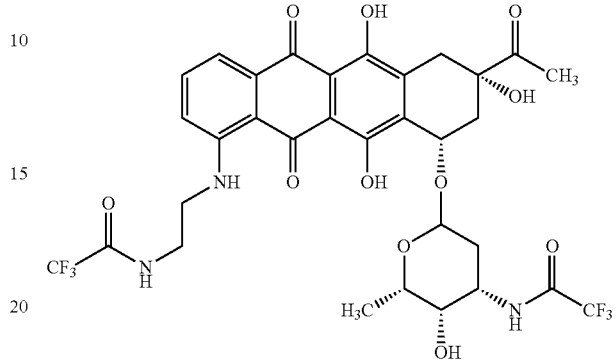

ESI MS: m/z 748 (MH$^+$)

(1S,3S)-3-acetyl-3,5,12-trihydroxy-10-[(2-hydroxyethyl)amino]-6,11-dioxo-1,2,3,4,6,11-hexahydrotetracen-1-yl 2,3,6-trideoxy-3-[(trifluoroacetyl)amino]-L-lyxo-hexopyranoside

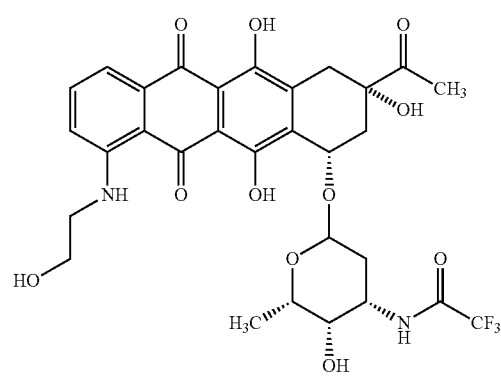 [SMILES: CC(=O)[C@]1(O)Cc2c(O)c3c(c(O)c2[C@@H](OC2C[C@H](NC(=O)C(F)(F)F)[C@H](O)[C@H](C)O2)C1)C(=O)c1c(NCCO)cccc1C3=O]

ESI MS: m/z 653 (MH$^+$)

Deprotection

The Title Compound (II)

The intermediate N-[(8S,10S)-8-acetyl-6,8,11-trihydroxy-5,12-dioxo-10-({2,3,6-trideoxy-3-[(trifluoroacetyl)amino]-α-L-lyxo-hexopyranosyl}oxy)-5,7,8,9,10,12-hexahydrotetracen-1-yl]-2,2,2-trifluoroacetamide (340.2 mg, 0.432 mmol) was cooled at 0° C. under argon and treated with a 0.1 N NaOH aqueous solution (12 mL). The reaction mixture was stirred in the dark at 0° C. for 1 hour, until no starting material was detectable (HPLC analysis). The reaction mixture was then diluted with DCM (50 mL), washed with saturated NaHCO$_3$ aqueous solution (3×30 mL), then with water (1×30 mL) and finally with saturated NaCl solution (1×30 mL). The organic phase was dried over anhydrous Na$_2$SO$_4$, the solvent was removed under vacuum affording the desired product (180.0 mg, red solid).

ESI MS: m/z 513 (MH$^+$)

$^1$H NMR (500 MHz, DMSO-d$_6$) δ pm 1.14 (d, J=6.52 Hz, 2H) 1.47 (dd, J=12.61, 4.33 Hz, 1H) 1.60 (d, J=3.30 Hz, 1H)

2.06-2.21 (m, 2H) 2.24-2.27 (m, 3H) 2.86 (d, J=12.58 Hz, 1H) 2.88-3.01 (m, 2H) 3.28 (br. s., 1H) 4.09 (d, J=6.29 Hz, 1H) 4.45 (br. s., 1H) 4.94 (t, J=4.22 Hz, 1H) 5.19 (d, J=3.53 Hz, 1H) 5.44 (s, 1H) 7.24 (d, J=8.28 Hz, 1H) 7.50 (d, J=7.13 Hz, 1H) 7.51-7.52 (m, 0H) 7.55-7.59 (m, 1H) 8.06 (br. s., 2H)

Analogously, by using the suitable starting material, the following compounds are prepared:

(1S,3S)-3-acetyl-10-[(2-aminoethyl)amino]-3,5,12-trihydroxy-6,11-dioxo-1,2,3,4,6,11-hexahydrotetracen-1-yl 3-amino-2,3,6-trideoxy-L-lyxo-hexopyranoside

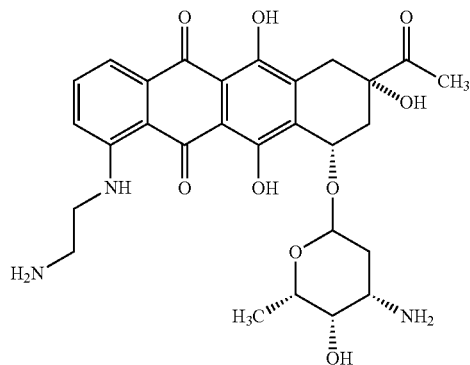 [SMILES: CC(=O)[C@]1(O)Cc2c(O)c3c(c(O)c2[C@@H](OC2C[C@H](N)[C@H](O)[C@H](C)O2)C1)C(=O)c1c(NCCN)cccc1C3=O]

ESI MS: m/z 556 (MH+)

(1S,3S)-3-acetyl-3,5,12-trihydroxy-10-[(2-hydroxyethyl)amino]-6,11-dioxo-1,2,3,4,6,11-hexahydrotetracen-1-yl 3-amino-2, 3,6-trideoxy-L-lyxo-hexopyranoside

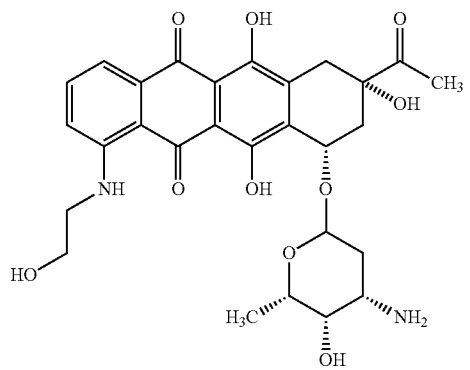 [SMILES: CC(=O)[C@]1(O)Cc2c(O)c3c(c(O)c2[C@@H](OC2C[C@H](N)[C@H](O)[C@H](C)O2)C1)C(=O)c1c(NCCO)cccc1C3=O]

ESI MS: m/z 557 (MH+)

The invention claimed is:
1. A compound of formula (I)

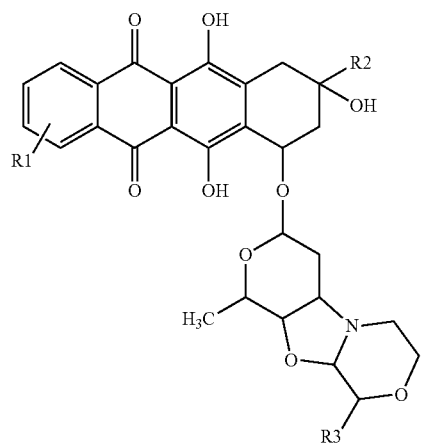

wherein:
R1 is halogen or NR4R5;
R2 is an optionally substituted group selected from straight or branched $C_2$-$C_6$ alkyl, NR7R8-$C_2$-$C_6$ alkyl, R6O—$C_2$-$C_6$ alkyl and COR9;
R3 is hydrogen or a straight or branched $C_1$-$C_4$alkoxy;
R4 and R5 are independently hydrogen, a monosubstituted-benzyl, a disubstituted-benzyl, or an optionally substituted group selected from straight or branched $C_1$-$C_6$ alkyl, NR7R8-$C_1$-$C_6$ alkyl, R6O—$C_1$-$C_6$ alkyl, R7R8N—$C_1$-$C_6$ alkylcarbonyl, R6O—$C_1$-$C_6$ alkylcarbonyl, R7R8N—$C_1$-$C_6$ alkylaminocarbonyl, R6O—$C_1$-$C_6$ alkylaminocarbonyl, R7R8N—$C_1$-$C_6$ alkylsulphonyl, R6O—$C_1$-$C_6$ alkylsulphonyl, R7R8N—$C_1$-$C_6$alkoxycarbonyl and R6O—$C_1$-$C_6$ alkoxycarbonyl; or
R4 and R5, taken together with the N atom to which they are bound, form a heterocyclyl substituted with R4;
R6, R7 and R8 are independently hydrogen or an optionally substituted straight or branched $C_1$-$C_6$ alkyl;
R9 is OR6, NR7R8 or an optionally substituted group selected from
straight or branched $C_1$-$C_4$ alkyl, NR7R8-$C_1$-$C_4$ alkyl and R6O—$C_1$-$C_4$ alkyl,
or a pharmaceutically acceptable salt thereof.
2. A compound of formula (Ia) or (Ib), according to claim 1,

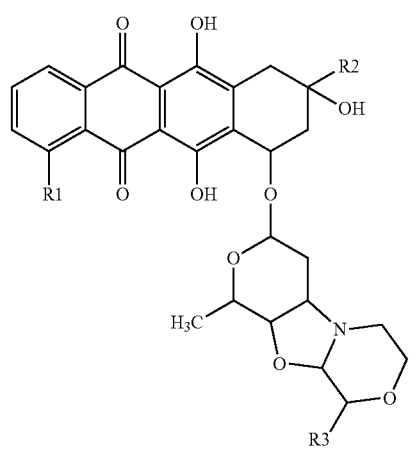

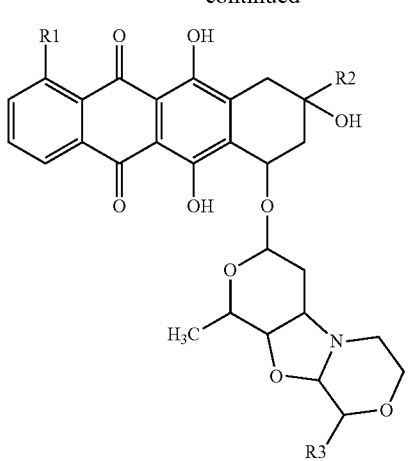

(Ib)

wherein R1 is fluorine or NR4R5, wherein one of R4 or R5 is hydrogen and the other is hydrogen or an optionally substituted group selected from straight or branched $C_1$-$C_6$ alkyl, NR7R8-$C_1$-$C_6$ alkyl, R6O—$C_1$-$C_6$ alkyl, R7R8N—$C_1$-$C_6$ alkylcarbonyl, R6O—$C_1$-$C_6$ alkylcarbonyl, R7R8N—$C_1$-$C_6$ alkylaminocarbonyl, R6O—$C_1$-$C_6$ alkylaminocarbonyl, R7R8N—$C_1$-$C_6$ alkoxycarbonyl and R6O—$C_1$-$C_6$ alkoxycarbonyl.

3. The compound of formula (Ia), according to claim 2, wherein R2 is COR9.

4. The compound of formula (Ia), according to claim 2, which is selected from the group consisting of:

(8S,10S)-8-acetyl-1-fluoro-6,8,11-trihydroxy-10-{[(1S,3R,4aS,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-1-fluoro-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-1-amino-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-8-acetyl-1-amino-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-8-acetyl-6,8,11-trihydroxy-1-[(2-hydroxyethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-6,8,11-trihydroxy-8-(hydroxyacetyl)-1-[(2-hydroxyethyl)amino]-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, (8S,10S)-8-acetyl-1-[(2-aminoethyl)amino]-6,8,11-trihydroxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione, and (8S,10S)-1-[(2-aminoethyl)amino]-6,8,11-trihydroxy-8-(hydroxyacetyl)-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione.

5. A pharmaceutical composition comprising a therapeutically effective amount of a compound of formula (I) or a pharmaceutically acceptable salt thereof, as defined in claim 1, and at least one pharmaceutically acceptable excipient, carrier or diluent.

6. A pharmaceutical composition according to claim 5, further comprising one or more chemotherapeutic agents.

7. A product comprising a compound of formula (I) or a pharmaceutically acceptable salt thereof, as defined in claim 1, and one or more chemotherapeutic agents, as a combined preparation for simultaneous, separate or sequential use in anticancer therapy.

8. A method for treating cancer, which comprises administering to a mammal in need thereof an effective amount of a compound of formula (I), as defined in claim 1.

9. The method of claim 8, wherein the mammal in need thereof is a human.

10. The method of claim 8, wherein the cancer is selected from the group consisting of bladder cancer, breast cancer, colon cancer, kidney cancer, liver cancer, lung cancer, small cell lung cancer, esophageal cancer, gall-bladder cancer, ovarian cancer, pancreatic cancer, stomach cancer, cervical cancer, thyroid cancer, prostate cancer, skin carcinoma, squamous cell carcinoma, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkitt's lymphoma, acute myelogenous leukemia, chronic myelogenous leukemia, myelodysplastic syndrome, promyelocytic leukemia, fibrosarcoma, rhabdomyosarcoma, astrocytoma, neuroblastoma, glioma, schwannoma, melanoma, seminoma, teratocarcinoma, osteosarcoma, xeroderma pigmentosum, keratoxanthoma, thyroid follicular cancer, Kaposi's sarcoma and mesothelioma.

11. A process for the preparation of a compound of formula (I) as defined in claim 1, which comprises:

first, reacting
the compound of formula (VII)

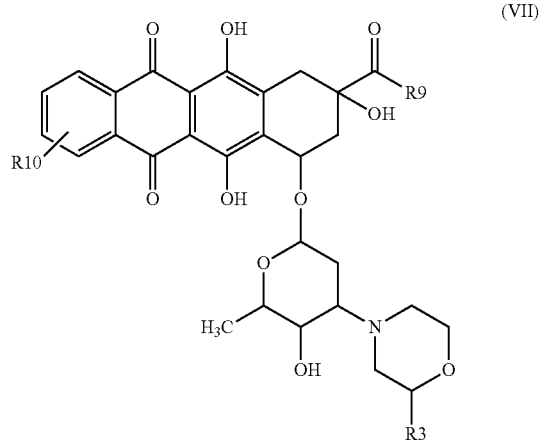

(VII)

wherein R3 and R10 are as defined in claim 1 and R9 is OR6 or NR7R8, wherein R6, R7 and R8 are as defined in claim 1, or
the compound of formula (VIII)

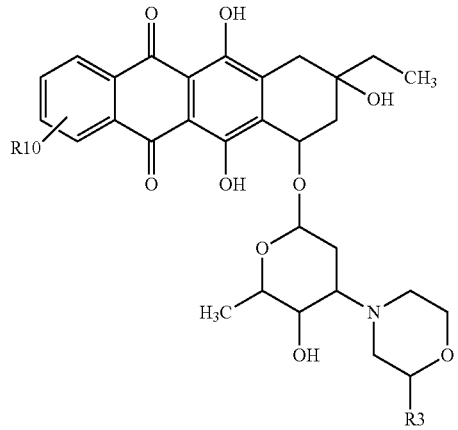

wherein R3 and R10 are as defined in claim 1,
or
the compound of formula (III)

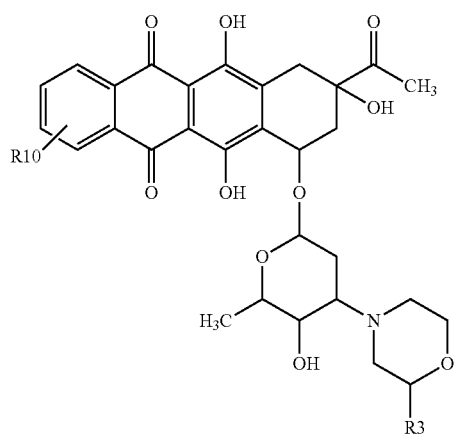

wherein R3 and R10 are as defined in claim 1, or
the compound of formula (IX)

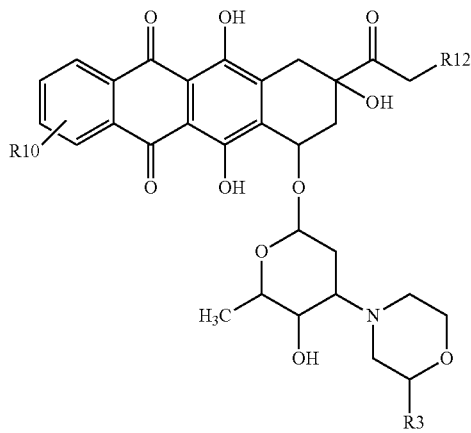

wherein R3 and R10 are as defined in claim 1, and R12 is group selected from straight or branched $C_1$-$C_4$ alkyl, NR7R8-$C_1$-$C_4$ alkyl and R60-$C_1$-$C_4$ alkyl,
or
the compound of formula (X)

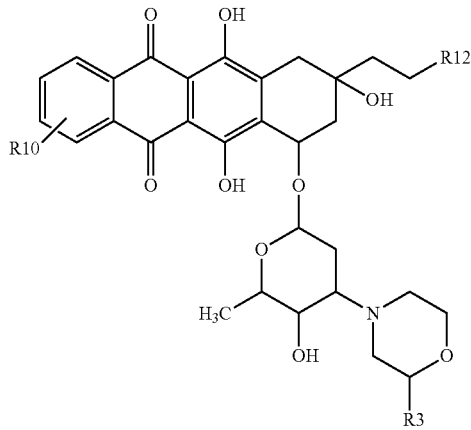

wherein R3, R10 and R12 are as defined in claim 1, or
the compound of formula (XI) or (XIa)
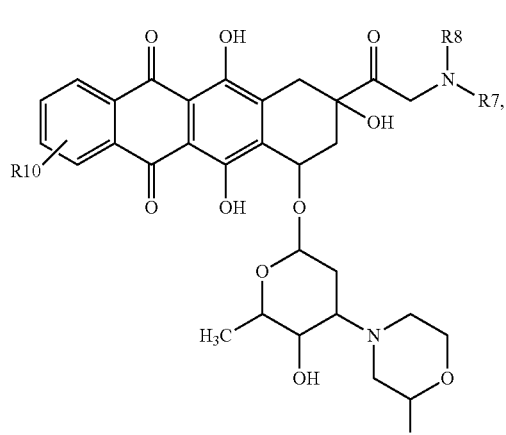
(XI)
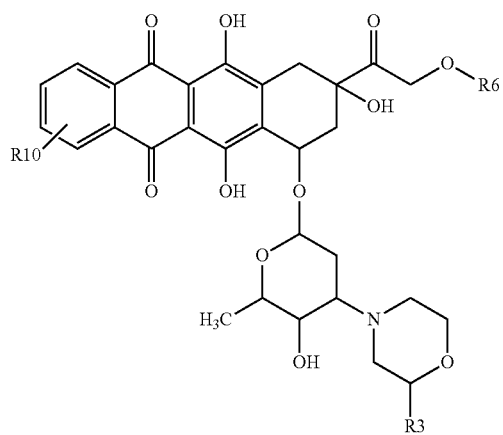
(XIa)
wherein R3, R6, R7, R8 and R10 are as defined in claim 1,
or
the compound of formula (XII) or (XIIa)
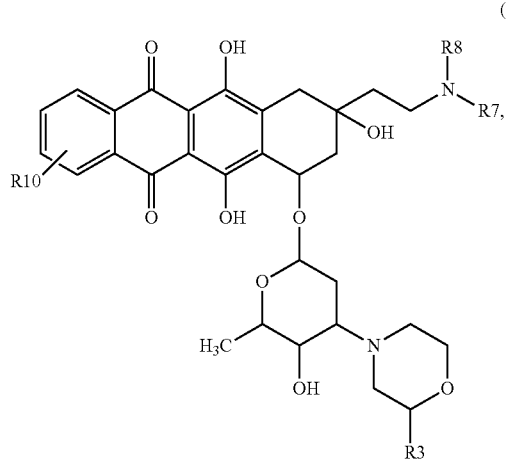
(XII)
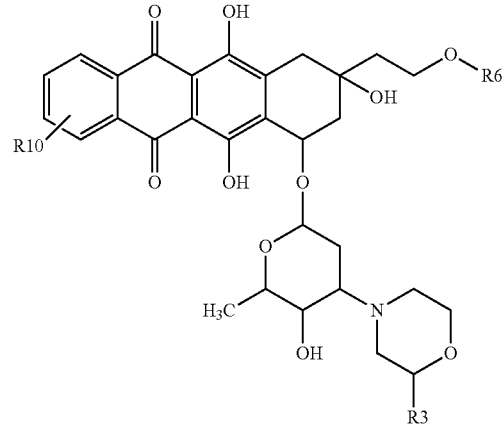
(XIIa)
wherein R3, R6, R7, R8 and R10 are as defined in claim 1,
or
the compound of formula (V)
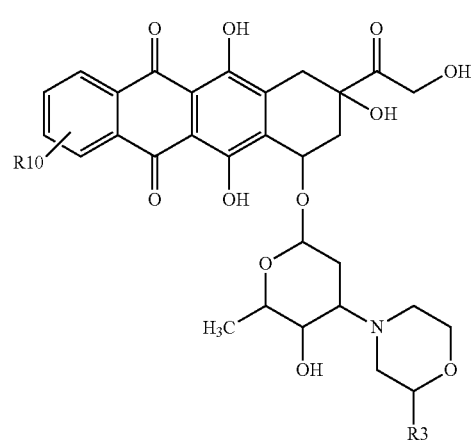
(V)
wherein R3 and R10 are as defined in claim 1,
or
the compound of formula (XIII)
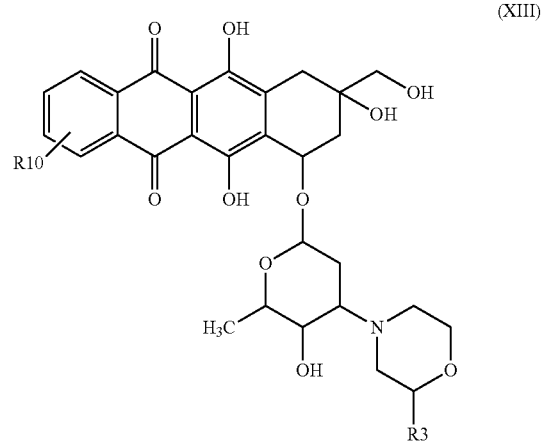
(XIII)
wherein R3 and R10 are as defined in claim 1, with DMDO;
then,
treating the resultant compound of formula (XX)

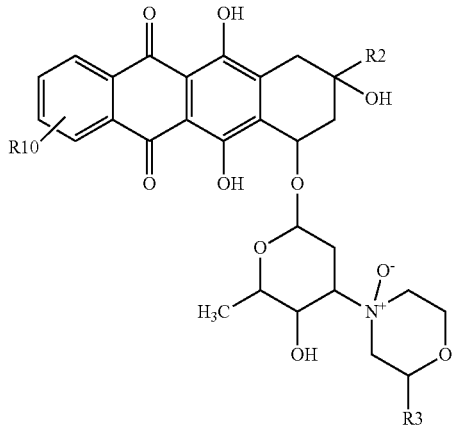

(XX)

wherein R3, R10 and R2 are as defined in claim 1, with cyanuric chloride or with an iron (II) salt, and finally, if desired removing the protecting group/s to obtain a compound of formula (I) as defined in claim 1, optionally converting a first compound of formula (I) into a second compound of formula (I) by known chemical reactions; and/or, if desired, converting such a compound of formula (I) into a pharmaceutically acceptable salt thereof or converting a salt into a free compound of formula (I).

* * * * *